US008849578B2

(12) United States Patent
Dobson et al.

(10) Patent No.: US 8,849,578 B2
(45) Date of Patent: *Sep. 30, 2014

(54) COMPUTATIONAL METHOD AND APPARATUS FOR PREDICTING POLYPEPTIDE AGGREGATION OR SOLUBILITY

(75) Inventors: Christopher Dobson, Cambridgeshire (GB); Fabrizio Chiti, Scandicci (IT); Jesus Zurdo, Cambridgeshire (GB)

(73) Assignee: Cambridge University Technical Services Ltd. (GB)

( * ) Notice: Subject to any disclaimer, the term of this patent is extended or adjusted under 35 U.S.C. 154(b) by 393 days.

This patent is subject to a terminal disclaimer.

(21) Appl. No.: 12/061,489

(22) Filed: Apr. 2, 2008

(65) Prior Publication Data

US 2008/0262742 A1  Oct. 23, 2008

Related U.S. Application Data

(60) Division of application No. 11/184,548, filed on Jul. 19, 2005, now Pat. No. 7,379,824, which is a continuation of application No. PCT/GB2004/000089, filed on Jan. 19, 2004.

(60) Provisional application No. 60/441,914, filed on Jan. 21, 2003.

(30) Foreign Application Priority Data

Jan. 20, 2003 (GB) .................................. 0301235.8

(51) Int. Cl.
G06F 19/00 (2011.01)
G06F 17/11 (2006.01)
G06F 19/16 (2011.01)
G06F 19/18 (2011.01)

(52) U.S. Cl.
CPC ................ G06F 19/16 (2013.01); G06F 19/18 (2013.01)
USPC .................... 702/19; 702/23; 702/27; 703/11

(58) Field of Classification Search
CPC .................................. G06F 19/16; G06F 19/18
See application file for complete search history.

(56) References Cited

U.S. PATENT DOCUMENTS

| 6,188,965 | B1 | 2/2001 | Mayo et al. |
|---|---|---|---|
| 6,269,312 | B1 | 7/2001 | Mayo et al. |
| 6,708,120 | B1 | 3/2004 | Mayo et al. |
| 7,379,824 | B2 | 5/2008 | Dobson et al. |
| 7,698,070 | B2 | 4/2010 | Dobson et al. |
| 7,930,157 | B2 | 4/2011 | Dobson |
| 2006/0025977 | A1 | 2/2006 | Dobson et al. |
| 2006/0271306 | A1 | 11/2006 | Dobson et al. |
| 2008/0183455 | A1 | 7/2008 | Dobson et al. |
| 2010/0261882 | A1 | 10/2010 | Doboson et al. |

FOREIGN PATENT DOCUMENTS

| EP | 1255209 | 11/2002 |
|---|---|---|
| WO | WO-0017328 A2 | 3/2000 |
| WO | WO-0242321 A2 | 5/2002 |
| WO | WO-2004066168 | 8/2004 |

OTHER PUBLICATIONS

Avbelj F. Journal of Molecular Biology, 300 (5), 2000, pp. 1335-1359.*
Dobson C. Phil. Trans. R. Soc. Lond. B 2001 356, 133-145.*
"U.S. Appl. No. 11/184,548, Amendment and Response filed Nov. 2, 2007 to Non-Final Office Action mailed Jul. 9, 2007", 7 pgs.
"U.S. Appl. No. 11/184,548, Response filed Apr. 9, 2007 to Restriction Requirement mailed Mar. 15, 2007", 13 pgs.
"U.S. Appl. No. 11/184,548, Restriction Requirement mailed Mar. 15, 2007", 6 pgs.
"U.S. Appl. No. 11/417,525, Final Office Action mailed Jul. 14, 2008", 10 pgs.
"U.S. Appl. No. 11/417,525, Non-Final Office Action mailed Feb. 11, 2009", 12 pgs.
"U.S. Appl. No. 11/417,525, Notice of Allowance mailed Nov. 25, 2009", 7 pgs.
"U.S. Appl. No. 11/417,525, Response filed Jul. 13, 2009 to Non Final Office Action mailed Feb. 11, 2009", 13 pgs.
"U.S. Appl. No. 11/417,525, Response filed Oct. 11, 2007 to Restriction Requirement mailed Sep. 11, 2007", 11 pgs.
"U.S. Appl. No. 11/417,525, Response filed Nov. 14, 2008 to Non-Final Office Action mailed Jul. 14, 2008", 10 pgs.
"U.S. Appl. No. 12/098,030, Non-Final Office Action mailed Apr. 30, 2010", 10 pgs.
"U.S. Appl. No. 12/098,030, Response filed Jan. 22, 2010 to Restriction Requirement mailed Dec. 22, 2009", 9 pgs.
"U.S. Appl. No. 12/098,030, Restriction Requirement mailed Dec. 22, 2009", 9 pgs.
"International Application No. PCT/GB2004,000089, Written Opinion mailed Jun. 23, 2004", 7 pgs.
Chiti, F., et al., "Kinetic partitioning of protein folding and aggregation", *Nature Structural Biology 9*,, (2002), 137-143.
"U.S. Appl. No. 11/184,548, Response filed Nov. 2, 2007 to Non-Final Office Action mailed Jul. 9, 2007", 9.
"U.S. Appl. No. 11/184,548, Notice of Allowance mailed Jan. 29, 2008", 4.
"U.S. Appl. No. 11/184,548,Supplemental Notice of Allowance mailed Mar. 12, 2008", SNOA,4.
"U.S. Appl. No. 11/417,525, Non-Final Office Action mailed Dec. 26, 2007", 11.

(Continued)

*Primary Examiner* — Michael Borin
(74) *Attorney, Agent, or Firm* — Schwegman Lundberg & Woessner, P.A.

(57) ABSTRACT

A prediction method for predicting the effect of an amino acid modification on the rate of aggregation (solubility) of a reference polypeptide comprising: calculating the difference in hydrophobicity ($\Delta$Hydr) between the reference polypeptide and a modified polypeptide, calculating the difference in $\beta$-sheet propensity ($\Delta\Delta G_{coil-\alpha}+\Delta\Delta G_{\beta-coil}$) between the reference polypeptide and modified polypeptide, calculating the difference in charge ($\Delta$ Charge) between the reference polypeptide and modified polypeptide, and calculating: [x*$\Delta$Hydr]+[y*($\Delta\Delta G_{coil-\alpha}+\Delta\Delta G_{\beta-coil}$)]−[z*$\Delta$ Charge], wherein x, y and z are scaling factors.

14 Claims, 8 Drawing Sheets

(56) References Cited

OTHER PUBLICATIONS

"U.S. Appl. No. 11/417,525, Restriction Requirement mailed Sep. 11, 2007", 8 pgs.

"U.S. Appl. No. 11/417,525, Amendment and Response filed Mar. 26, 2008 to Office Action mailed Dec. 26, 2007", 12.

"International Search Report for corresponding PCT Application No. PCT/GB2004/000089", (Jun. 23, 2004),5 pgs.

Chiti, et al., *PNAS*, vol. 99, Suppl. 4, (Dec. 10, 2002), 16419-16426.

Qamar, S. , et al., "Probing the Determinations of Protein Solubility with Amino Acid Modification", *J. of Boichem*; 114(6), Japanese Biotechnology Society,(1993),786-792.

"U.S. Appl. No. 11/184,548, Preliminary Amendment filed Jul. 19, 2005", 3 pgs.

"U.S. Appl. No. 12/098,030, Notice of Allowance mailed Dec. 9, 2010", 7 pgs.

"U.S. Appl. No. 12/098,030, Preliminary Amendment filed Apr. 4, 2008", 3 pgs.

"U.S. Appl. No. 12/098,030, Response filed Sep. 30, 2010 to Non Final Office Action mailed Apr. 30, 2010", 15 pgs.

"U.S. Appl. No. 12/719,631, Non Final Office Action mailed Jun. 15, 2011", 10 pgs.

"U.S. Appl. No. 12/719,631, Response filed Apr. 14, 2011 to Restriction Requirement mailed Mar. 15, 2011", 6 pgs.

"U.S. Appl. No. 12/719,631, Restriction Requirement mailed Mar. 15, 2011", 7 pgs.

U.S. Appl. No. 11/184,548, Response filed Nov. 2, 2007 to Non-Final Office Action mailed Jul. 9, 2007, 9.

U.S. Appl. No. 11/184,548, Notice of Allowance mailed Jan. 29, 2008, 4.

U.S. Appl. No. 11/184,548, Supplemental Notice of Allowance mailed Mar. 12, 2008, SNOA,4.

U.S. Appl. No. 11/417,525, Non-Final Office Action mailed Dec. 26, 2007, 11.

U.S. Appl. No. 11/417,525, Restriction Requirement mailed Sep. 11, 2007, 8 pgs.

U.S. Appl. No. 11/417,525, Amendment and Response filed Mar. 26, 2008 to Office Action mailed Dec. 26, 2007, 12.

International Search Report for corresponding PCT Application No. PCT/GB2004/000089, (Jun. 23, 2004),5 pgs.

Avbel, J. , et al., *Journal of Molecular Biology* 300 (5), (2000),1335-135.

Avbelj, F. , "Amino Acid Conformational Preferences and Solvation of Polar Backbone Atoms in Peptides and Proteins", *Journal of Molecular Biology*, 300(5), (Jul. 28, 2000),1335-1359.

Broome, et al., *Journal of Molecular Biology* 296 (4), (Mar. 3, 2000),961-968.

Chiti, et al., *PNAS*, vol. 99, Suppl. 4, (Dec. 10, 2002),16419-16426.

Qamar, S., et al., "Probing the Determinations of Protein Solubility with Amino Acid Modification", *J. of Biochem*; 114(6), Japanese Biotechnology Society, (1993), 786-792.

Avbel, J., et al., *Journal of Molecular Biology 300* (5), (2000),1335-135.

Avbelj, F., "Amino Acid Conformational Preferences and Solvation of Polar Backbone Atoms in Peptides and Proteins", *Journal of Molecular Biology*,300(5), (Jul. 28, 2000),1335-1359.

Avbelj, F., et al., "Role of Main-Chain Electrostatics, Hydrophobic Effect and Side-Chain Conformational Entropy in Determining the Secondary Structure of Proteins", *Journal of Molecular Biology*, 279(3), (Jun. 12, 1998),665-684.

De La Paz, M. L., et al., "De novo Designed Peptide-Based Amyloid Fibrils", *Proc Natl Acad Sci USA.*, 99(25), (Dec. 10, 2002),16052-16057.

Qamar, et al., *J. Biochem*, vol. 114 (6), (1993),786-79.

Siepen, J. A., et al., "The fibril_one On-line Database: Mutations, Experimental Conditions, and Trends Associated With Amyloid Fibril Formation", *Protein Science*, 11, (Jul. 2002),1862-1866.

\* cited by examiner

SEQUENCE LISTING

```
<160> NUMBER OF SEQ ID NOS: 14

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000
```

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 32
<212> TYPE: PRT
<213> ORGANISM: Artificial Sequence
<220> FEATURE:
<223> OTHER INFORMATION: A synthetic oligopeptide

```
<400> SEQUENCE: 14

Cys Gly Asn Leu Ser Thr Cys Met Leu Gly Lys Leu Thr Gln Glu Leu
 1               5                  10                  15

Arg Lys Leu His Thr Phe Pro Gln Thr Ala Ile Gly Val Gly Ala Pro
                20                  25                  30
```

COMPUTATIONAL METHOD AND APPARATUS FOR PREDICTING POLYPEPTIDE AGGREGATION OR SOLUBILITY

RELATED APPLICATIONS

This application is a divisional of U.S. patent application Ser. No. 11/184,548, filed Jul. 19, 2005, which is a continuation under 35 U.S.C. 111(a) of PCT/GB2004/000089, filed Jan. 19, 2004 and published as WO 2004/066168 A1, filed Aug. 5, 2004, which claimed priority under 35 U.S.C. 119 to United Kingdom Application No. 0301235.8, filed Jan. 20, 2003, and under 35 U.S.C. 119(e) to United States Provisional patent application No. 60/441,914, filed Jan. 21, 2003, which applications and publication are incorporated herein by reference and made a part hereof.

TECHNICAL FIELD

This invention relates to methods for determining the effect of an amino acid modification on the rate of aggregation of a polypeptide by calculating the propensity of a modified polypeptide to aggregate, i.e. the solubility of a modified polypeptide, relative to a reference polypeptide. The invention further relates to a method for designing a modified polypeptide with a particular ability to aggregate, i.e. a particular solubility. The invention further relates to such methods carried out by means of computer software and to computer hardware programmed for carrying out the methods.

BACKGROUND ART

An understanding of the effects of peptide and protein modifications, such as amino acid substitutions, on the propensities of specific polypeptides to aggregate is of crucial importance for elucidating the molecular basis of protein deposition diseases, such as Alzheimer's and other amyloid diseases, and for understanding the mechanisms of action of the mutations associated with hereditary forms of such diseases.

In each of the various pathological conditions associated with protein and peptide deposition, a specific peptide or protein that is normally soluble is deposited, either intact or in fragmented form, into insoluble aggregates that accumulate in one or more type(s) of tissue. Numerous mutations have been found to be associated with familial forms of protein deposition diseases and more than 100 have been shown directly to involve the sequence of the peptide or protein responsible for aggregation (Siepen and Westhead, 2002). Many of these mutations have been identified over the past 5 years, and the number is expected to increase dramatically in the near future. Investigation of the mechanisms by which natural mutations result in pathological behaviour has proved to be of fundamental importance for exploring the molecular basis of the underlying disease, even in those cases where they are sporadic rather than familial in origin (Selkoe, 2001; Volles & Lansbury, 2002).

The ability to form highly organised aggregates having common structural characteristics, such as amyloid, has been found to be a generic property of polypeptides, regardless of sequence or structural similarity, and not simply a feature of small numbers of proteins associated with recognised pathological conditions (Dobson, 2001).

In the native state, hydrophobic residues are usually embedded within the core of a protein, thus the opportunity for these residues to interact is limited. However, proteins are dynamic and an equilibrium exists between the stable and folded conformation, and destabilised, partially or fully unfolded states. The free energy value ($\Delta G$, kJ mol$^{-1}$) for a protein provides an indication of the stability of the protein. Aggregation occurs when proteins in their native state denature; as the protein unfolds, intramolecular bonds are broken, allowing the polypeptide main chain (backbone) and hydrophobic side chains to be exposed. Hydrogen bonds and other interactions can then form between the partially or fully denatured protein molecules, resulting in intermolecular associations and aggregate formation.

In some instances, it may be desirable to form aggregates, in particular fibrils, for example for use as plastic materials, in electronics, as conductors, for catalysis or as a slow release form of the polypeptide, or where polypeptide fibrils are to be spun into a polypeptide "yarn" for various applications; for example, as described in published patent applications WO0017328 (Dobson) and WO0242321 (Dobson & McPhee).

However, in other circumstances the formation of aggregates is disadvantageous, for example, when it is desired to use a polypeptide at concentrations or under conditions desirable for physiological activity, therapeutic administration or industrial application. In particular, the use of bioactive peptides and proteins as pharmaceutical agents is limited where the peptide or protein tends to form aggregates during manufacture, processing, storage or following administration. These issues are widely recognised in the biotechnological and pharmaceutical industry and constitute a major problem and economic burden, that can be difficult to overcome and may require the use of sophisticated expression and refolding techniques, the development of specific formulations, stabilising agents and excipients, cold chain delivery, or immediate reconstitution before use. Almost all known polypeptide therapeutic products present these problems, e.g. insulin, interferon-γ, BMPs, calcitonin, glucagon, antibodies.

Various factors are known to affect the tendency of a polypeptide to aggregate. Some of these factors are local to amino acid residues, other factors are global and can affect the entire protein. For example, when mutations are made in a polypeptide, local factors in the region of the mutation such as increased hydrophobicity, or tendency to convert from α-helix to β-sheet conformation, result in a higher rate of aggregation than that of the wild type (non-mutant) protein. "Global" or overall changes due to mutations can also affect the rate of aggregation; for example, a change in net charge of the mutant polypeptide bringing it closer to neutral results in an increased tendency of a polypeptide to aggregate. Mutations that destabilise the native state of the polypeptide also result in facilitated aggregation.

A detailed mutational study on a model protein, muscle acylphosphatase (AcP), demonstrated that the rate of aggregation from an ensemble of partially denatured conformations can be followed readily for AcP using a variety of spectroscopic probes. The rate of aggregation was determined for over 50 mutational variants of this protein (Chiti et al., 2002a; 2002b: Chiti, P., Taddei, N., Baroni, F., Capanni, C., Stefani, M., Ramponi, G. & Dobson, C. M. Kinetic partitioning of protein folding and aggregation. *Nature Struct. Biol.* 9, 137-143 (2002a); Chiti, F., Calamai, M., Taddei, N., Stefani, M. Ramponi, G. & Dobson, C. M. Studies of the aggregation of mutant proteins in vitro provide insights into the genetics of amyloid diseases. *Proc. Natl. Acad. Sci. USA*, 99: 16419-16426 (2002b)). Many of these mutations, particularly those involving residues 16-31 and 87-98, were found to perturb the aggregation rate of AcP very significantly (Chiti et al., 2002a; 2002b). Chiti (2002a) concluded that the measured changes in aggregation rate upon mutation positively correlated with changes in the hydrophobicity and β-sheet propensity of the regions of the protein in which the mutations are located. Chiti (2002b) examined AcP mutations that altered the charge state of the AcP protein without affecting significantly the hydrophobicity or secondary structure propensities of the polypeptide chain. An inverse correlation was reported between the rate of aggregation of protein variants under denaturing conditions and the overall net charge of the protein.

The factors that affect the rate of aggregation of a protein are diverse. When amino acid substitutions are made in a protein, several factors are involved to different extents. A single mutation can increase the net charge, thereby disfavouring aggregation (for example, the replacement of Ala for Asp in a positively charged protein). Nevertheless, the same mutation can increase hydrophobicity, thereby bringing an accelerating contribution to the aggregation rate. Finally, the same mutation also changes the α-helical and β-sheet propensities of the polypeptide chain, introducing other factors. The relationship between the factors and their relative importance to aggregation (solubility) are not well characterised.

Thus, it has not been possible to predict accurately the tendency of a protein to form insoluble and ordered aggregates, such as amyloid fibrils, nor to predict or calculate the effect of specific amino acid modifications, such as replacements, on aggregation/solubility. The inability to make such predictions or calculations constitutes a problem in the design and/or handling of polypeptides, whether in vivo or in vitro.

The ability to predict the intrinsic effects of mutations on polypeptide aggregation is of crucial importance in elucidating the pathogenic effect of the large numbers of mutations associated with protein deposition diseases. It would be desirable to establish, in specific cases, whether a given mutation would give rise to the disease as a direct result of its effect on the aggregation process of the polypeptide involved, or by other mechanisms. In addition, the establishment of general principles in aggregation would make it possible to use statistical methods to analyse the relationships between mutation, aggregation and disease. An understanding of the effects of amino acid substitutions on the propensities of specific proteins to aggregate would allow the establishment of criteria to modify rationally the aggregational properties of natural or designed peptides and proteins for industrial processes, research purposes, medical treatment or biotechnological application. Furthermore, methods of the invention may be used to identify or design polypeptide sequences with a reduced aggregation propensity, re-designed polypeptides could be administered by methods such as gene therapy to treat certain disorders, particularly those associated with protein aggregation. The ability to identify or design polypeptides with specific aggregation properties will be important for development and manufacture of polypeptides for applications in the material and device areas, such as those described in WO0017328 (Dobson) and WO0242321 (Dobson & McPhee).

It would therefore be useful to be able to predict if a particular polypeptide would form insoluble aggregates and to predict the effect that a particular modification or modifications of amino acid sequence would have on the aggregation/solubility properties of a polypeptide.

DISCLOSURE OF INVENTION

The invention provides a prediction method for predicting the effect of an amino acid modification on the rate of aggregation (solubility) of a reference polypeptide, which method comprises calculating the difference in hydrophobicity ($\Delta$Hydr) between the reference polypeptide and a modified polypeptide, calculating the difference in β-sheet propensity ($\Delta\Delta G_{coil-\alpha}+\Delta\Delta G_{\beta-coil}$) between the reference polypeptide and modified polypeptide, calculating the difference in charge ($\Delta$ Charge) between the reference polypeptide and modified polypeptide and calculating: $[x^*\Delta\text{Hydr}]+[y^*(\Delta\Delta G_{coil-\alpha}+\Delta\Delta G_{\beta-coil})]-[z^*\Delta \text{ Charge}]$, wherein x, y and z are scaling factors. A value for $[x^*\Delta\text{Hydr}]+[y^*(\Delta\Delta G_{coil-\alpha}+\Delta\Delta G_{\beta-coil})]-[z^*\Delta \text{ Charge}]$ of a first sign indicates that the modified polypeptide has a greater propensity to aggregate relative to the reference polypeptide and a value for $[x^*\Delta\text{Hydr}]+[y^*(\Delta\Delta G_{coil-\alpha}+\Delta\Delta G_{\beta-coil})]-[z^*\Delta \text{ Charge}]$ of a sign opposite to the first sign indicates that the modified polypeptide has a reduced propensity to aggregate relative to the reference polypeptide. If the effect of the amino acid modification on the rate of aggregation is expressed as $\ln(v_{mod}/v_{ref})$, a positive value for $\ln(v_{mod}/v_{ref})$, indicates that the modified polypeptide has a greater propensity to aggregate (lower solubility) relative to the reference polypeptide; and a negative value for $\ln(v_{mod}/v_{ref})$, indicates that the modified polypeptide has a reduced propensity to aggregate (higher solubility) relative to the reference polypeptide.

In a preferred method the scaling factor x is a value from 0.59 to 0.64 to, the scaling factor y is a value from 0.19 to 0.22 and the scaling factor z is a value from 0.49 to 0.51. It is particularly preferred that the scaling factor x is 0.6, 0.63 or 0.633, the scaling factor y is 0.2 or 0.198 and the scaling factor z is 0.5, 0.49 or 0.491.

The invention also provides an identification method for identifying an amino acid modification that reduces the aggregation rate (increases the solubility) of a reference polypeptide comprising using a method of the invention to predict the change in aggregation rate for one or more modified polypeptide(s), the modified polypeptide having one or more amino acid modification(s) when compared to the reference polypeptide, comparing the predicted aggregation rates of the reference and said one or more modified polypeptides, and identifying one or more modified polypeptide(s) having a predicted reduced aggregation rate relative to the reference polypeptide. In another aspect, the present invention provides a modified polypeptide having a reduced aggregation rate identified by this method. The invention further provides a prediction method as hereinbefore described for use in the identification method or in the preparation of a modified polypeptide The invention also provides an identification method for identifying an amino acid modification that increases the aggregation rate (decreases the solubility) of a polypeptide comprising using a method of the invention to predict the change in aggregation rate for one or more modified polypeptide(s), each modified polypeptide having one or more amino acid modification(s) when compared to the reference polypeptide, comparing the predicted aggregation rates of the reference and said one or more modified polypeptide(s) and identifying one or more modified polypeptides having a predicted increased aggregation rate relative to the reference polypeptide. Additionally, the present invention provides a modified polypeptide having an increased aggregation rate identified by this method.

A method is provided for making a polypeptide having a reduced aggregation rate (increased solubility) comprising using a method of the invention to identify a modification predicted to reduce the aggregation rate of a polypeptide and making a modified polypeptide having said modification.

Also provided is a modified polypeptide having a reduced aggregation rate obtained by this method.

A method is provided for making a polypeptide having an increased aggregation rate (decreased solubility) comprising using a method of the invention to identify a modification predicted to increase the aggregation rate of a polypeptide and making a modified polypeptide having said modification. Another aspect of the invention provides a modified polypeptide having an increased aggregation rate obtained by this method.

In an aspect of the invention the reference and modified polypeptide(s) are structurally related in terms of amino acid composition and sequence. Structurally related polypeptides have at least 60%, preferably at least 70%, more preferably at least 80%, yet more preferably at least 90%, further preferably at least 95% amino acid sequence homology. In an alternative aspect, the reference and modified polypeptide(s) are structurally unrelated. Preferably the reference polypeptide is a wild type polypeptide and the modified polypeptide is a mutant thereof. A modified polypeptide is preparable by chemical modification and/or by modification(s) such as substitution, deletion and/or addition of one or more amino acids of the reference protein. An amino acid substituted or added to the reference protein may be a natural amino acid or a chemically synthesised or chemically modified amino acid. Preferably 1 to 20, 1 to 16, 1 to 12, or 1 to 10 amino acids are substituted, deleted and/or added; most preferably 1, 2, 3, 4, 5, or 6 amino acids are substituted, deleted and/or added. Preferably, the modification of the polypeptide is by amino acid substitution, which can be substitution of one or more amino acids, preferably by substitution of 1 to 20, 1 to 16, 1 to 12, or 1 to 10 amino acids, more preferably substitution of 1, 2, 3, 4, 5, or 6 amino acids. Alternatively, modification the polypeptide may be by deletion of one or more amino acids, preferably by deletion of 1 to 20, 1 to 16, 1 to 12, or 1 to 10 amino acids; more preferably by deletion of 1, 2, 3, 4, 5, or 6 amino acids.

The reference polypeptide may be a natural polypeptide from any species, or a non-natural "designed" polypeptide. Proposed modifications of the reference polypeptide may be selected by comparing the amino acid sequence of a reference polypeptide with the amino acid sequence of a related polypeptide or polypeptides from different species. It is preferred that modification be made in regions of a polypeptide that are polymorphic between different species. Proposed modifications of a reference protein may also be selected by comparing the amino acid sequence of the reference protein with naturally occurring or induced polypeptide variants of the reference protein, preferably by comparing wild type and mutant polypeptides.

The reference polypeptide is preferably a human polypeptide. Proposed modifications of a human reference polypeptide may be selected by comparing a human reference polypeptide with a related polypeptide from a non-human source. Modification may be such that an amino acid in the human form of a polypeptide is modified to the amino acid present at that position in a related polypeptide from a non-human source. Alternatively, the reference polypeptide may be a non-human polypeptide and the modification may be such that the non-human polypeptide is "humanised".

For bioactive polypeptides, it is preferred that modification is such that an activity of the polypeptide is maintained or improved. The modification may be outside the active site of the polypeptide or may be within the active site of the polypeptide.

The term polypeptide as used herein encompasses proteins and peptides.

Using the methods of the invention, the intrinsic effects of specific modifications, such as mutations, on the rates of aggregation of polypeptides can be rationalised and predicted to a remarkable extent on the basis of simple physical principles: the effects that the modifications have on the fundamental parameters of hydrophobicity and secondary structure propensity at the site of modification, and on charge of the molecule as a whole. Based on this calculation, modified (e.g. mutant) polypeptides can be designed that are more/less liable to aggregate (that have a lesser or greater solubility) than the reference (e.g. wild type) polypeptide, or that have a propensity to aggregate within a desired range. Thus it is possible to assess the effects that various amino acid modifications will have on the properties of a polypeptide without having to make modified polypeptides and measure experimentally the effect of the changes. Design of massive numbers of modified polypeptides is feasible, even for a relatively short reference polypeptide. This is important because modifications can be selected also to fulfil other criteria or restrictions, such as protein stability, function etc.

The change of aggregation rate as a result of a modification (e.g. mutation) can be expressed as $\ln(v_{mod}/v_{ref})$, e.g. ($\ln(v_{mut}/v_{wt})$). The rate of aggregation may also be expressed in terms of an aggregation time, such as a half time of aggregation, and a ratio of aggregation rate is equivalent to a ratio of aggregation times, as discussed further later.

The kinetic parameters for aggregation can be aggregation rates corresponding to an exponential kinetic of aggregation (v) or, when a time parameter ($\tau$) is used, $(\tau_{mod}/\tau_{ref})=(v_{ref}/v_{mod})=1/\exp(\ln(v_{mod}/v_{ref}))$, can include or refer exclusively to nucleation stages and/or "lag phases" of the aggregation kinetics (T1) or to the half-time of aggregation of the overall process (T2).

Change of hydrophobicity ($\Delta$Hydr) is calculated using $\Delta$Hydr=Hydr$_{ref}$−Hydr$_{mod}$, where $\Delta$Hydr is the change of hydrophobicity that would result from a proposed amino acid modification, Hydr$_{ref}$ and Hydr$_{mod}$ are the hydrophobicity values of the reference and modified amino acid residues, respectively.

A consensus hydrophobicity scale can be used to assign a hydrophobicity value for each amino acid. Different hydrophobicity scales may be used for different pH values, for example, scales described in Cowan, R. & Whittaker, R. G. (1990) Peptide Research 3: 75-80) may be used to calculate the hydrophobicity of polypeptides at low pH. An averaged hydrophobicity scale can be used, which can be obtained by using a combination of scales, such as those available in the literature (e.g. Fauchere J.-L & Pliska V. E. (1983) Eur. J. Med. Chem. 18: 369-375; Kyte J., Doolittle R. F. (1982) J. Mol. Biol. 157: 105-132). In a preferred embodiment, the hydrophobicity value for each amino acid is assigned using the values given in Table 1 for hydrophobicity of the 20 amino acid residues at neutral pH based on the partition coefficients from water to octanol; the data are from column 6 of Table 4.8 in Creighton (1993) (Creighton, T. E. In *Proteins. Structure aid molecular properties. Second edition.* W. H. Freeman & Company (New York, 1993), p. 154.).

The scaling factor x can be derived by plotting observed $\ln(v_{mod}/v_{ref})$, e.g. $\ln(v_{mut}/v_{wt})$, versus $\Delta$Hydr for a number of polypeptide sequences, which may be unrelated or related (e.g. a collection of AcP mutants) and determining the line of best fit, the scaling factor x is the slope (gradient) of the line.

To calculate propensity to convert from α-helical to β-sheet structure ($\Delta\Delta G_{coil-\alpha}+\Delta\Delta G_{\beta-coil}$), individual values for $\Delta\Delta G_{coil-\alpha}$ and $\Delta\Delta G_{\beta-coil}$ are calculated.

$\Delta\Delta G_{coil-\alpha}$ can be calculated using: $\Delta\Delta G_{coil-\alpha}=RT \ln(P_\alpha^{ref}/P_\alpha^{mod})$, where $\Delta\Delta G_{coil-\alpha}$ is the predicted change of free energy for the transition from α-helix to random coil resulting from modification; R=0.008314 kJ mol$^{-1}$ K$^{-1}$, $P_\alpha^{ref}$ and $P_\alpha^{mod}$ are respectively the predicted α-helical propensities (helix percentages) of the reference (e.g. wild type) and modified (e.g. mutant) sequences at the site of amino acid modification, respectively. The predicted α-helical propensities can be calculated using modelling software/algorithms such as AGADIR (www.embl-heidelberg.de/Services/serrano/agadir/agadir-start.html) Muñoz & Serrano (1994) Nature Structural Biol 1, 399-409; Muñoz & Serrano (1994) J Mol Biol 245, 297-308; Muñoz & Serrano (1997) Biopolymers 41 495 509 and Lacroix et al (1998) J Mol Biol 284 173-191; PHD (Rost, B. et al, (1993) J Mol Biol 232, 584-599); PROF (Rost, B. et al, (1996) Methods Enzymol 266, 525-539); GOR4 (Garnier J et al (1978) J Mol Biol 120, 97-120; Garnier J et al (1996) Methods Enzymol 266, 540-553). Any suitable algorithms based on structural databases, structural preference databases or rotamer preference databases could be used for this calculation to estimate helical propensities, for example, GOR IV: J. Garnier. J. F. Gibrat and B. Robson in Methods Enzymol., vol 266, p 540-553 (1996). J. Garnier, D. Osguthorpe and B. Robson (J. Mol. Biol. 120, 97, 1978). J Mol Biol 1987 Dec. 5; 198(3):425-443 (GOR-III); PHD: Rost B, Sander C. J Mol Biol 1993 Jul. 20; 232(2):584-99. Rost B, Sander C. Proteins 1994 May; 19(1):55-72; PREDATOR Frishman D, Argos P. Protein Eng 1996 February; 9(2):133-142; SIMPA/SIMPA96: Levin J M, Robson B, Garnier J. FEBS Lett 1986 Sep. 15; 205(2):303-308. J. LEVIN, J. GARNIER. Biochim. Biophys. Acta, (1988) 955, 283-295. Levin J M. Protein Eng. (1997), 7, 771-776. SOPM/SOPMA Geourjon C, Deleage G. Protein Eng 1994 February; 7(2):157-164. Geourjon C, Deleage G. Comput Appl Biosci 1995 December; 11(6):681-684.

$\Delta\Delta G_{\beta\text{-}coil}$ can be calculated using: $\Delta\Delta G_{\beta\text{-}coil}=13.64\ (P_\beta^{ref}-P_\beta^{mod})$, where $\Delta\Delta G_{\beta\text{-}coil}$ is the change of free energy for the transition from random coil to β-sheet resulting from the modification ($\Delta G_{\beta\text{-}coil}$), 13.64 is the conversion constant from the normalised scale to units of kJ mol$^{-1}$; $P_\beta^{ref}$ and $P_\beta^{mod}$ are the normalised β-sheet propensities of the reference (e.g. wild type) and modified (e.g. mutant) residue, respectively. Values of β-sheet propensity for all 20 amino acids can be determined using a published scale. A preferred scale is given in Table 1, which provides β-sheet propensity values for 19 amino acid residues (all except proline), these are normalised from 0 (high β-sheet propensity) to 1 (low β-sheet propensity). These data are from column 4 of Table 1 of Street and Mayo (1999) (Street, A. G. & Mayo, S. L. Intrinsic β-sheet propensities result from van der Waals interactions between side chains and the local backbone. Proc. Natl. Acad. Sci. USA, 96, 9074-9076 (1999)). The β-sheet propensity of proline is not reported due to the difficulty in determining it experimentally. The β-sheet propensity of glycine is obtained from theoretical calculations.

The scaling factor y can be derived by plotting observed $\ln(v_{mod}/v_{ref})$ versus $(\Delta\Delta G_{coil\text{-}\alpha}+\Delta\Delta G_{\beta\text{-}coil})$ for a number of unrelated or related polypeptide sequences (e.g. by plotting observed $\ln(v_{mut}/v_{wt})$ versus $(\Delta\Delta G_{coil\text{-}\alpha}+\Delta\Delta G_{\beta\text{-}coil})$ for a number of AcP polypeptide mutations) and determining the line of best fit, the scaling factor y is the slope (gradient) of the line.

Change of charge (ΔCharge) of the polypeptide is calculated using:
ΔCharge=|Charge$_{mod}$|−|Charge$_{ref}$|, where ΔCharge is the change of charge resulting from the mutation, |Charge$_{mod}$| and |Charge$_{ref}$| are the absolute values of charge for the modified (e.g. mutant) and reference (e.g. wild-type) sequences, respectively (obtained from the sums of the charge values for amino acid residues (e.g. the values given in Table 1, which are at neutral pH). The operator of "absolute value" is introduced so that a negative value of ΔCharge results from the equation when the mutation causes the entire protein or peptide to approach neutrality, regardless of the initial sign of the protein sequence. A positive value of ΔCharge is obtained when the mutation causes the entire protein sequence to deviate further from neutrality.

The scaling factor z can be derived by plotting observed $\ln(v_{mod}/v_{ref})$ versus ΔCharge for a number of related or unrelated polypeptide sequences, e.g. by plotting observed $\ln(v_{mut}/v_{wt})$ for a number of AcP polypeptide mutants, and determining the line of best fit; the scaling factor z is the slope (gradient) of the line.

The scaling factors x, y, and z can be refined by plotting a larger number of data points for further polypeptide modifications. A multiple regression analysis can be used to determine the scaling factors x for ΔHydr, y for $\Delta\Delta G_{coil\text{-}\alpha}+\Delta\Delta G_{\beta\text{-}coil}$, and z for Δ Charge. The multiple regression analysis method consists of calculating simultaneously the individual scaling factors x, y, and z for a given set of polypeptides (e.g. mutant polypeptides) for which the experimental values of $\ln(v_{mod}/v_{ref})$ (e.g. $\ln(v_{mut}/v_{wt})$) are available. Initial estimations for the values of x, y and z, such as the values described herein or values chosen on an arbitrary basis, can be used in the calculations. The calculated $\ln(v_{mod}/v_{ref})$ values are compared with the values obtained experimentally. The calculations can be repeated through a number of iterations, each time using a different combination of x, y, and z values. The iterations will end when a set of best values is found for x, y and z, i.e. when minimal difference between the calculated and experimental value of $\ln(v_{mod}/v_{ref})$ is found.

The calculation can be modified by inclusion of another term or terms, such as a stability factor to correct for mutations that affect protein stability. Terms can be added to the equation to represent other factors that affect aggregation rate, such as the position of the mutation along the sequence, non-cumulative effects of double substitutions, distance in sequence between double substitutions. Refinement of the equation by inclusion of additional factors can improve the accuracy of the method. Accordingly, methods of the invention can further comprise an additional calculation step or steps, for example, an additional step in which a stability factor is used to correct for mutations that affect protein stability.

The invention also provides computer program code to, when running, predict the effect of an amino acid modification on the rate of aggregation of a polypeptide, the code comprising code to: input an amino acid modification that would convert the reference polyeptide to a modified form of the polypeptide; calculate a difference in hydrophobicity (ΔHydr) between the reference polypeptide and modified polypeptide; calculate a difference in β-sheet propensity ($\Delta\Delta G_{coil\text{-}\alpha}+\Delta\Delta G_{\beta\text{-}coil}$) between the reference polypeptide and modified polypeptide; calculate a difference in charge (Δ Charge) between the reference polypeptide and modified polypeptide; and calculate: [x*ΔHydr]+[y*($\Delta\Delta G_{coil\text{-}\alpha}+\Delta\Delta G_{\beta\text{-}coil}$)]−[z*Δ Charge], wherein x, y and z are scaling factors.

We also describe computer program code to, when running, identify a polypeptide, the code comprising: code to predict the change in aggregation rate for one or more modified polypeptides, comprising code as described above; and further code to identify one or more of said modified polypeptides dependent upon said predicted change in aggregation rate.

The invention also provides a computer system for determining a rate of aggregation of a second polypeptide in relation to a reference polypeptide, said second polypeptide and said reference polypeptide each having an amino acid sequence, the amino acid sequence of said second polypeptide comprising a modified version of the amino acid sequence of said reference polypeptide, the computer system comprising a data store for storing data comprising hydrophobicity data, β-sheet propensity data and charge data for a set of amino acids; a program store storing processor implementable code; and a processor, coupled to said program store and to said data store for implementing said stored code, the code comprising code for controlling the processor to: input an amino acid sequence for said second polypeptide; read hydrophobicity data for said second polypeptide amino acid sequence from said data store and determine a hydrophobicity value for said second polypeptide; read change data for said second polypeptide amino acid sequence from said data store and determine a β-sheet propensity value for said second polypeptide; determine an α-helix propensity value for said second polypeptide; obtain hydrophobicity data, charge data, β-sheet propensity data and an α-helix propensity value for said reference polypeptide; and determine said relative rate of aggregation using said hydrophobicity, change, β-sheet and α-helix propensity data for said second and reference polypeptide. The terms "second polypeptide" and "modified polypeptide" are used interchangeably.

In an embodiment the β-sheet propensity may be expressed in terms of free energy. The set of amino acids may comprise, for example, all the natural amino acid residues. The α-helix propensities of the reference and modified polypeptide sequences may be determined using a code within the computer system or a request may be sent to a separate computer system, for example on a network, and α-helix propensity data received back from this second computer system. The hydrophobicity data, charge data and secondary structural propensity data for the reference and modified polypeptides may be determined from scales of values for each amino acid that were previously published and input to the computer system and/or stored, for example in the data store. The relative rate of aggregation determined by the apparatus may simply comprise a determination of whether the aggregation rates (or in other embodiments, the solubility) of the second polypeptide is above or below that of the reference polypeptide; alternatively a quantitative determination of the relative aggregation rates of these polypeptides may be made. Preferably the code evaluates the sum of a difference in hydrophobicity, a difference in secondary structural propensity and a difference in charge between the second polypeptide and the reference polypeptide, each multiplied by a scaling factor. One or more of the scaling factors may be selected responsive to, for example, the type of polypeptide for which the determination is being made.

The computer system may be used to evaluate a plurality of second polypeptides, presenting the results, for example, as an ordered list or graph and/or selecting a promising candidate sequence for synthesis and further evaluation.

In a further aspect the invention provides a method of determining a relative aggregation rate indicator, said relative aggregation rate indicator predicting a rate of aggregation of a second polypeptide in comparison to a rate of aggregation of a reference polypeptide, said second polypeptide comprising a version of said reference polypeptide with a modified amino acid sequence, the method comprising: determining a difference in hydrophobicity between said second polypeptide and said reference polypeptide; determining a difference in a secondary structure propensity between said second polypeptide and said reference polypeptide; determining a difference in charge between said second polypeptide and said reference polypeptide; forming a weighted combination of said difference in hydrophobicity, said difference in secondary propensity of said difference in change to determine said relative aggregation rate indicator.

The invention further provides computer programme code to implement the above-described methods, and computer apparatus programmed to implement the methods. Embodiments of the methods may be implemented using computer programme code in peptide synthesis apparatus, preferably apparatus for automatically synthesising a polypeptide based upon results obtained by applying the methods. The invention also encompasses polypeptides synthesised in this manner.

The program code may be provided on a data carrier or storage medium, such as a hard or floppy disk, ROM or CD-ROM, or on an optical or electrical signal carrier, for example via a communications network. The processor control code may comprise program code in any conventional programming language for example C or assembler or machine code, and embodiments of the invention may be implemented on a general purpose computer system.

EXAMPLES

Example 1

AcP Experimental Work

Figure 1A:
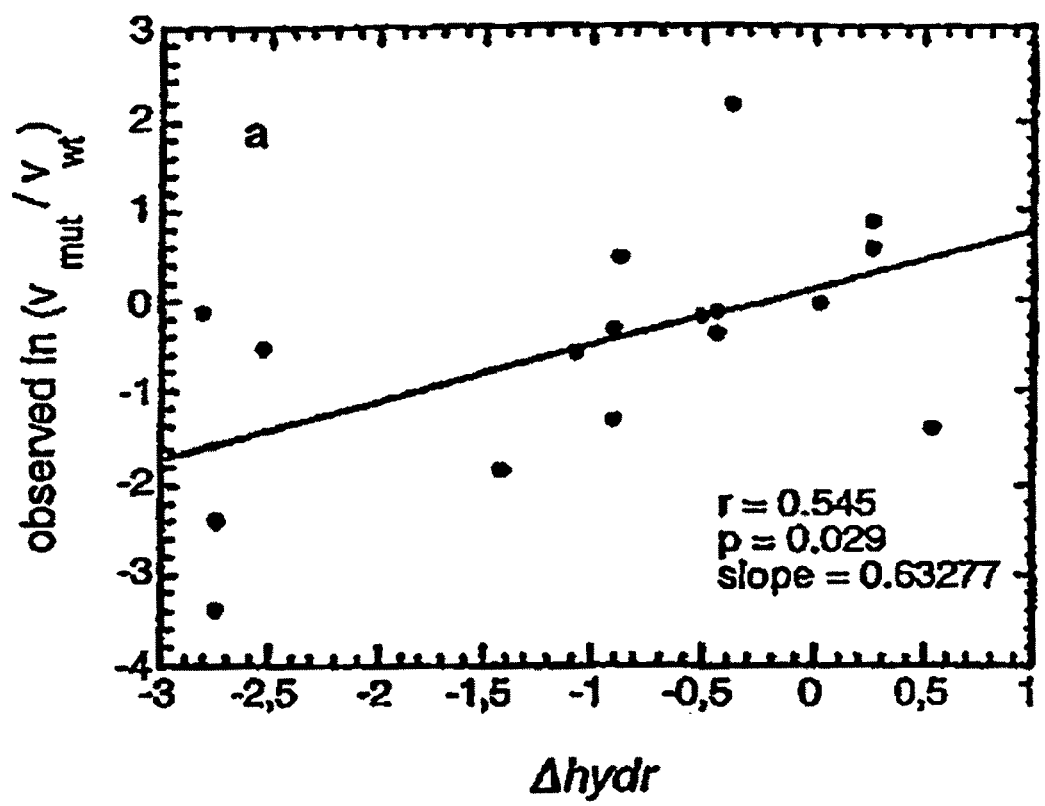
FIG. 1 shows the change of the aggregation rate of AcP resulting from mutation plotted against (a) the predicted change of hydrophobicity, (b) propensity to convert from an α-helical to a β-sheet conformation and (c) charge.

The rates of aggregation for wild type AcP protein ($v_{wt}$) and for various AcP mutants (variants) ($v_{mut}$) were measured upon denaturation in 25% TEM, from time courses of ThT fluorescence, as described by Chiti et al., 2002a (Chiti, F., Taddei, N., Baroni, F., Capanni, C., Stefani, M., Ramponi, G. & Dobson, C. M. Kinetic partitioning of protein folding and aggregation. *Nature Struct. Biol.* 9, 137-143 (2002a)). All aggregation rate measurements were carried out under conditions in which all protein variants consist of ensembles of relatively unstructured conformations. The change of aggregation rate as a result of a mutation was expressed in all cases as the natural logarithm of the ratio of the aggregation rate constants of the mutant and wild-type protein ($\ln(v_{mut}/v_{wt})$).

In Table 1, the hydrophobicity values of the 20 amino acid residues at neutral pH are based on the partition coefficients from water to octanol. These data are from column 6 of Table 4.8 in Creighton (1993) (Creighton, T. E. In *Proteins. Structure and molecular properties. Second edition*. W. H. Freeman & Company (New York, 1993), p. 154.)). The β-sheet propensities of the 20 amino acid residues are normalised from 0 (high β-sheet propensity) to 1 (low β-sheet propensity). These data are from column 1 of Table 4 of Street and Mayo (1999) (Street, A. G. & Mayo, S. L. Intrinsic β-sheet propensities result from van der Waals interactions between side chains and the local backbone. *Proc. Natl. Acad. Sci. USA*, 96, 9074-9076 (1999)). The β-sheet propensity of proline is not reported due to the difficulty in determining it experimentally. The β-sheet propensity of glycine is obtained from theoretical calculations. The values of charge are at neutral pH. Values in brackets are at a pH lower than 6.0, when the histidine residue is positively charged.

TABLE 1

Scales of hydrophobicity, β-sheet propensity and charge for the 20 natural amino acids

| amino acid residue | hydrophobicity (kJ mol$^{-1}$) | β-sheet propensity | charge |
|---|---|---|---|
| Arg (R) | 3.95 | 0.35 | +1 |
| Lys (K) | 2.77 | 0.34 | +1 |
| Asp (D) | 3.81 | 0.72 | −1 |
| Glu (E) | 2.91 | 0.35 | −1 |
| Asn (N) | 1.91 | 0.40 | 0 |
| Gln (Q) | 1.30 | 0.34 | 0 |
| His (H) | 0.64 (2.87) | 0.37 | 0 (+1) |
| Ser (S) | 1.24 | 0.30 | 0 |
| Thr (T) | 1.00 | 0.06 | 0 |
| Tyr (Y) | −1.47 | 0.11 | 0 |
| Gly (G) | 0.00 | 0.60 | 0 |
| Pro (P) | −0.99 | n.d. | 0 |
| Cys (C) | −0.25 | 0.25 | 0 |
| Ala (A) | −0.39 | 0.47 | 0 |
| Trp (W) | −2.13 | 0.24 | 0 |
| Met (M) | −0.96 | 0.26 | 0 |
| Phe (F) | −2.27 | 0.13 | 0 |
| Val (V) | −1.30 | 0.13 | 0 |
| Ile (I) | −1.82 | 0.10 | 0 |
| Leu (L) | −1.82 | 0.32 | 0 |

Using the data in Table 1, the change of hydrophobicity (ΔHydr), propensity to convert from α-helical to β-sheet structure ($\Delta\Delta G_{coil-\alpha} + \Delta\Delta G_{\beta-coil}$) and change of charge (ΔCharge) were quantified for AcP using the tabulated values for all the amino acid residues.

The change in hydrophobicity (ΔHydr) resulting from mutation was calculated using $\Delta\text{Hydr} = \text{Hydr}_{wt} - \text{Hydr}_{mut}$, where $\text{Hydr}_{wt}$ and $\text{Hydr}_{mut}$ are the hydrophobicity values of the wild type and mutant residues, respectively (the values of hydrophobicity for all 20 amino acids are listed in Table 1).

To calculate the propensity to convert from α-helical to β-sheet structure ($\Delta\Delta G_{coil-\alpha} + \Delta\Delta G_{\beta-coil}$), it was necessary to calculate $\Delta\Delta G_{coil-\alpha}$ and $\Delta\Delta G_{\beta-coil}$.

The change of free energy for the transition random coil→β-sheet resulting from mutation ($\Delta\Delta G_{\beta-coil}$) was calculated using $\Delta\Delta G_{\beta-coil} = 13.64\,(P_\beta^{wt} - P_\beta^{mut})$. $P_\beta^{wt}$ and $P_\beta^{mut}$ are the normalised β-sheet propensities of the wild-type and mutant residue, respectively (the values of β-sheet propensity for all 20 amino acids are listed in Table 1), and 13.64 is the conversion constant from the normalised scale to units of kJ mol$^{-1}$.

The predicted change of free energy for the transition α-helix→random coil resulting from mutation ($\Delta\Delta G_{coil-\alpha}$) was calculated using $\Delta\Delta G_{coil-\alpha} = RT\,\ln(P_\alpha^{wt}/P_\alpha^{mut})$. $P_\alpha^{wt}$ and $P_\alpha^{mut}$ are the predicted α-helical propensities (helix percentages) of the wild type and mutated sequences at the site of mutation, respectively which were calculated using the AGADIR algorithm at www.embl-heidelberg.de/Services/serrano/agadir/agadir-start.html); R=0.008314 kJ mol$^{-1}$ K$^{-1}$. (see also Lacroix, E., Viguera A R & Serrano, L. (1998). J. Mol. Biol. 284, 173-191).

The change of charge resulting from the mutation (ΔCharge) was calculated using $\Delta\text{Charge} = |\text{Charge}_{mut}| - |\text{Charge}_{wt}|$, where $|\text{Charge}_{wt}|$ and $|\text{Charge}_{mut}|$ are the absolute values of charge for the wild-type and mutated sequences, respectively (obtained from the sums of the charge values of all residues reported in Table 1).

Figure 1B:
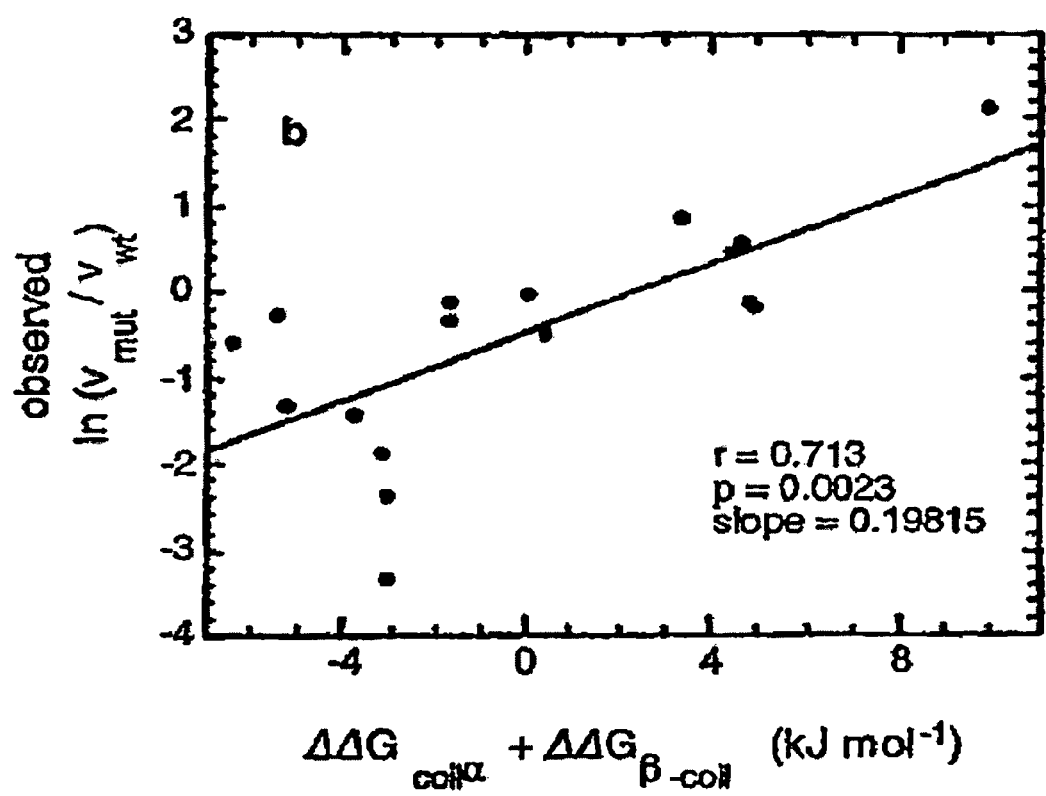
Figure 1C:
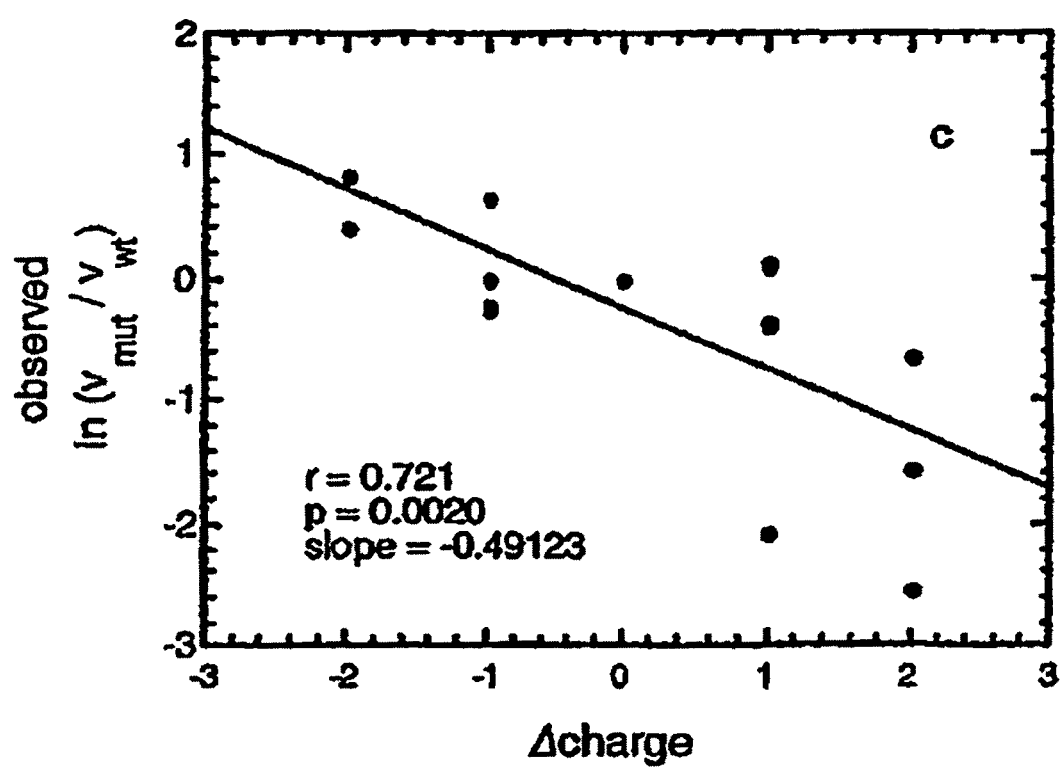

The change of aggregation rate upon mutation $\ln(v_{mut}/v_{wt})$ was plotted individually against ΔHydr, against ($\Delta\Delta G_{coil-\alpha} + \Delta\Delta G_{\beta-coil}$) and against ΔCharge, these plots are shown in FIGS. 1a, 1b and 1c, respectively.

The mutations reported in FIGS. 1a and 1b, described previously (Chiti et al., 2002a, ibid.), do not involve change of charge. The mutations reported in FIG. 1c, described previously (Chiti et al., 2002b, ibid.), were designed to minimise change of hydrophobicity and secondary structure propensities. Most of the amino acid substitutions of AcP involve residues within the two regions of the sequence, encompassing residues 16-31 and 87-98, that are thought to be relevant for aggregation.

The solid lines through the data represent the best fits to linear functions. The r and p values resulting from each correlation and the slope of the best fits are shown in each case.

In each of the analyses, the data points are considerably scattered around the lines representing the best fits to linear functions. This scatter can be attributed to the fact that only a single parameter is considered in each case, to the difficulty in predicting accurately changes in the hydrophobicity and secondary structure propensities, and to the varying relative importances of the different sites of mutation in the aggregation process. Despite the scatter present in each plot, however, the change of aggregation rate upon mutation ($\ln(v_{mut}/v_{wt})$) for AcP was found to correlate significantly with each of these parameters individually (FIGS. 1a, 1b, and 1c). The Despite the scatter present in each plot, however, the change of aggregation rate upon mutation ($\ln(v_{mut}/v_{wt})$) for AcP was found to correlate significantly with each of these parameters individually FIGS. 1a, 1b, and 1c). Average dependency of $\ln(v_{mut}/v_{wt})$ on each parameter was calculated (the slope of the line of best fit resulting from each analysis. The values were found to be:

ΔHydr 0.633

$\Delta\Delta G_{coil-\alpha} + \Delta\Delta G_{\beta-coil}$ 0.198

ΔCharge 0.491

Following this analysis, Equation 1 was devised and used to determine the change of aggregation rate upon mutation ($\ln(v_{mut}/v_{wt})$ value):

$\ln(v_{mut}/v_{wt}) = 0.633 * \Delta\text{Hydr} + 0.198 * (\Delta\Delta G_{coil-\alpha} + \Delta\Delta G_{\beta-coil}) - 0.491 * \Delta\text{Charge}$ where the numbers preceding the parameters of ΔHydr, ($\Delta\Delta G_{coil-\alpha} + \Delta\Delta G_{\beta-coil}$) and ΔCharge are values for x, y and z respectively that correspond to the slopes of the three plots reported in FIG. 1 (i.e. the dependencies of $\ln(v_{mut}/v_{wt})$ on the three parameters).

Example 2

Comparison of Observed Versus Calculated Change in Aggregation Rate on Mutation of AcP Protein/Relative Aggregation Rates of Mutant AcP Proteins

Using Equation 1, the change of aggregation rate $\ln(v_{mut}/v_{wt})$ was calculated for 27 amino acid substitutions of AcP within the two regions of the sequence that appear to be relevant for aggregation and encompassing residues 16-31 and 87-98. The change of aggregation rate for each mutation was determined experimentally, as described in Example 1, under conditions in which all protein variants consist of ensembles of relatively unstructured conformations. The calculated versus the experimental values of $\ln(v_{mod}/v_{wt})$ for all the mutations of AcP were plotted as shown in FIG. 2b. The observed correlation was found to be highly significant (r=0.756 and p<0.0001) and the slope was close to 1.

Example 3

Comparison of Observed Versus Calculated Change in Rate of Aggregation on Mutation for a Range of Polypeptides

The combined function, Equation 1, was applied to calculate the change in aggregation rate upon mutation (calculated $\ln(v_{mod}/v_{wt})$) for 26 mutations in the polypeptides amylin, prion peptides, α-synuclein, amyloid β-peptide, tau, leucine rich repeat and a model peptide, as listed in Table 2.

Values for ΔHydr, $\Delta\Delta G_{coil-\alpha}+\Delta\Delta G_{\beta-coil}$ and ΔCharge were calculated for each polypeptide mutation using the methods described in Example 1.

The 26 mutations considered included both physiologically relevant mutations associated with genetic forms of protein deposition diseases and other substitutions that had been used in research to address specific issues. They were all mutations of either unstructured proteins (peptides), or polypeptides that appear to be natively unfolded, such as the amyloid β peptide, the islet amyloid polypeptide, α-synuclein, tau, short peptides dissected from the sequence of the prion protein and other model peptides. Only single-point mutations within short unstructured peptides or proteins that are unfolded under conditions close to physiological were considered in the analysis. All mutations were included for which actual experimental values of $\ln(v_{mod}/v_{wt})$ were directly available or could be determined from data in the literature. Mutations that acted simply by destabilising the native state of the protein involved were excluded. Data were considered regardless of the experimental techniques employed by the different authors to probe aggregation, provided a quantitative analysis could be carried out. When time or rate constants were not explicitly reported, the plots describing the kinetic profiles of aggregation were scanned and computer-analysed. This procedure allowed plots with numerical values of the data points to be reconstructed and analysed to obtain rate constant values. When lag and growth phases were evident in the kinetic profiles of aggregation, only the growth phase was considered. When data at fixed periods of time were reported (for example by means of bar graphs), the value for observed $\ln(v_{mut}/v_{wt})$ value was obtained from the ratio of the aggregation parameters of the mutated and wild-type protein (peptide), before equilibrium was reached.

Mutations involving proline residues were not analysed because of the difficulty in obtaining quantitative estimates of the change of β-sheet propensity as a result of these mutations (see Table 1). Nor were mutations considered when substantial discrepancies in the $\ln(v_{mut}/v_{wt})$ value were reported by different authors (when significant but not substantial discrepancies were present, we considered $\ln(v_{mut}/v_{wt})$ values resulting from averages of the available data).

TABLE 2

Changes of hydrophobicity, secondary structure propensities, charge and aggregation rate as a result of single-point mutations of unstructured peptides or natively unfolded proteins.

| Mutation | ΔHydr (kJ mol$^{-1}$) | $\Delta\Delta G_{\beta-coil}$ (kJ mol$^{-1}$) | $\Delta G_{coil-\alpha}$ (kJ mol$^{-1}$) | ΔCharge | calculated $\ln(v_{mut}/v_{wt})$ | observed $\ln(v_{mut}/v_{wt})$ | ref. |
|---|---|---|---|---|---|---|---|
| amylin |  |  |  |  |  |  |  |
| N22A | 2.30 | −0.95 | −3.36 | 0 | 0.60 | 0.69 | 11 |
| F23A | −1.88 | −4.64 | −3.90 | 0 | −2.88 | −2.65 | 11 |
| G24A | 0.39 | 1.77 | −2.84 | 0 | 0.04 | −0.03 | 11 |
| I26A | −1.43 | −5.05 | −0.32 | 0 | −1.97 | −2.39 | 11 |
| L27A | −1.43 | −2.05 | 0.36 | 0 | −1.24 | −0.93 | 11 |
| S20G | 1.24 | −4.09 | 0.00 | 0 | −0.03 | 1.01 | 12 |
| prion peptides |  |  |  |  |  |  |  |
| H111A | 3.26 | −1.36 | −3.21 | −1 | 1.65 | 0.60 | 13 |
| H111K | 0.10 | 0.41 | −1.72 | 0 | −0.20 | −0.26 | 13 |
| A117V | 0.91 | 4.63 | 2.37 | 0 | 1.96 | 1.51 | 13 |
| V210I | 0.52 | 0.41 | −0.97 | 0 | 0.22 | 0.84 | 14 |
| α-synuclein |  |  |  |  |  |  |  |
| A53T | −1.39 | 5.59 | 2.83 | 0 | 0.79 | 1.18 | 15 |
| A76E | −3.30 | 1.64 | 0.00 | 1 | −2.25 | −2.72 | 16 |
| A76R | −4.34 | 1.64 | 0.64 | −1 | −1.80 | −0.93 | 16 |
| Amyloid-β peptide |  |  |  |  |  |  |  |
| A21G | −0.39 | −1.77 | 3.27 | 0 | 0.05 | −0.07 | 17 |
| E22K | 0.14 | 0.14 | −1.72 | −2 | 0.76 | 0.92 | 18 |
| E22Q | 1.61 | 0.14 | 0.00 | −1 | 1.54 | 2.92 | 17, 18 |
| E22G | 2.91 | −3.41 | 4.30 | −1 | 2.51 | 2.03 | 19 |

TABLE 2-continued

Changes of hydrophobicity, secondary structure propensities, charge and aggregation rate as a result of single-point mutations of unstructured peptides or natively unfolded proteins.

| Mutation | $\Delta$Hydr (kJ mol$^{-1}$) | $\Delta\Delta G_{\beta\text{-}coil}$ (kJ mol$^{-1}$) | $\Delta G_{coil\text{-}\alpha}$ (kJ mol$^{-1}$) | $\Delta$Charge | calculated $\ln(v_{mut}/v_{wt})$ | observed $\ln(v_{mut}/v_{wt})$ | ref. |
|---|---|---|---|---|---|---|---|
| D23N | 1.90 | 4.36 | −1.72 | −1 | 2.22 | 3.97 | 17 |
| F19T | −3.27 | 0.95 | −1.76 | 0 | −2.23 | −2.48 | 20 |
| Tau | | | | | | | |
| G272V | 1.30 | 6.41 | −1.71 | 0 | 1.75 | 1.04 | 21, 22 |
| R406W | 6.08 | 1.50 | 0.00 | −1 | 4.64 | 1.25 | 21, 22, 23 |
| Y310W | 0.66 | −1.77 | 0.00 | 0 | 0.07 | 0.05 | 23bis |
| Leucine-rich repeat | | | | | | | |
| D24N | 1.90 | 4.36 | −3.43 | −1 | 1.88 | 2.08 | 24 |
| D24Q | 2.51 | 5.18 | −3.10 | −1 | 2.49 | 1.25 | 24 |
| Model peptide | | | | | | | |
| D6E | 0.90 | 5.04 | −2.27 | 0 | 1.12 | 0.40 | 25 |
| D6N | 1.90 | 4.36 | 0.00 | 1 | 1.57 | 0.52 | 25 |

Figure 2A:
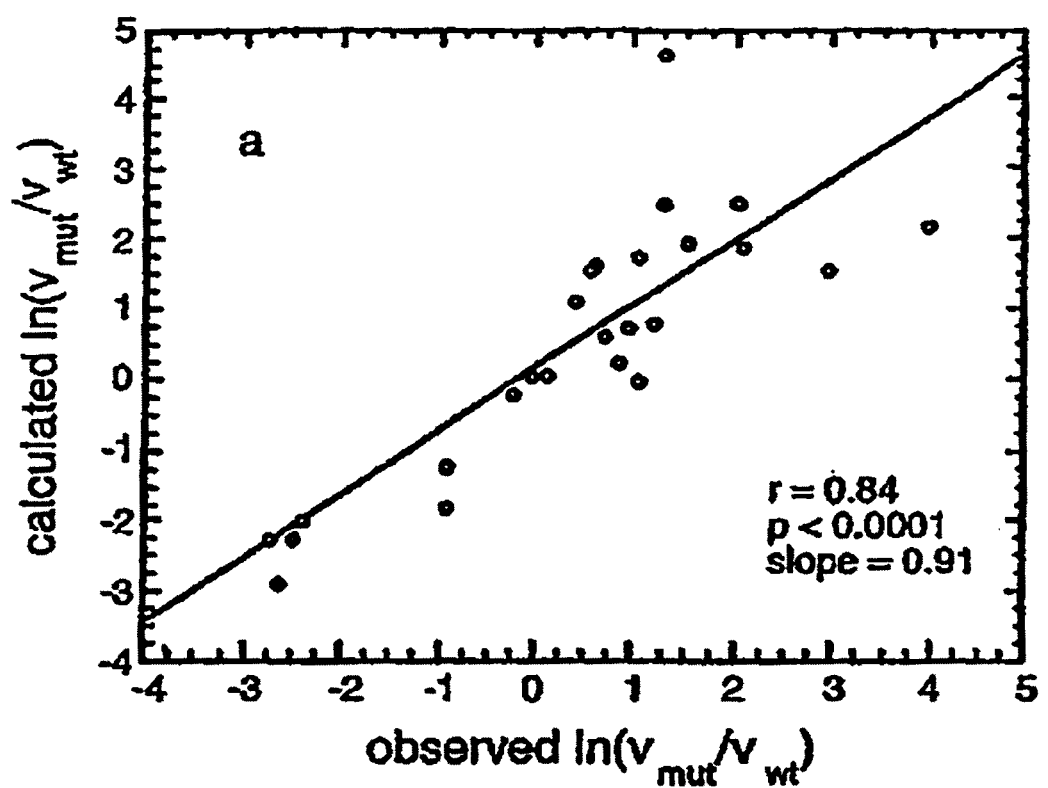
FIG. 2(a) shows the calculated versus observed change of the aggregation rate upon mutation for the short peptides or natively unfolded proteins listed in Table 2.
Figure 2B:
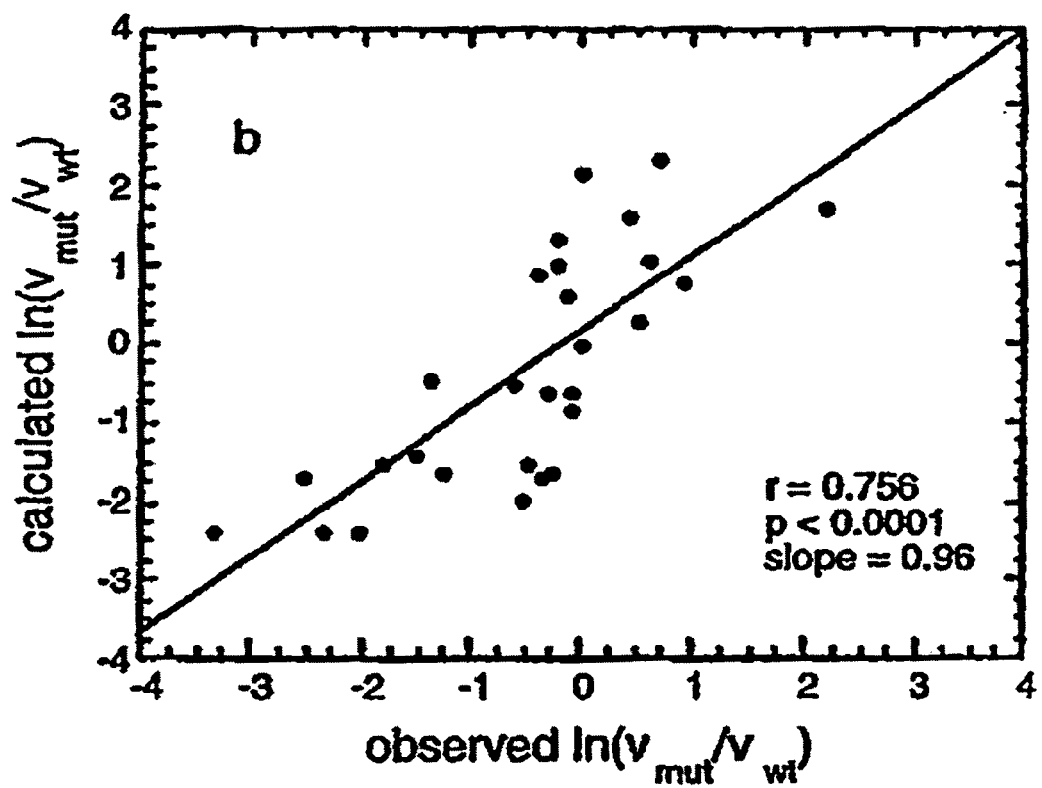
FIG. 2(b) shows the calculated versus observed change of the aggregation rate upon mutation for 27 amino acid substitutions of AcP within two regions of the sequence that appear to be relevant for aggregation and encompassing residues 16-31 and 87-98.

The calculated versus the experimental value of $\ln(v_{mut}/v_{wt})$ was plotted and is shown in FIG. 2(a). The highly significant correlation (r=0.84, p<0.0001), and the value of the slope that is close to 1.0, indicate close agreement between calculated and experimental effects of mutations on the aggregation rates of this heterogeneous group of polypeptides. The observed changes of aggregation rate upon mutation span a range of ca. 800 times, i.e. from 15 slower to 53 faster than the corresponding wild-type polypeptide (FIG. 2a and Table 2). 84% of these mutations have calculated values of $\ln(v_{mut}/v_{wt})$ that vary within a factor of 3 from the observed values of $\ln(v_{mod}/v_{wt})$. The percentage rises to 92% and 96% if spread factors of 5 and 10 are considered, respectively. Examples where close agreement is found between theoretical and experimental values include mutations associated with hereditary spongiform endephalopathies, such as the A117V and V210I substitutions of the prion protein (Table 2). Predicted and experimental values are in close agreement also for the A53T mutation associated with early-onset Parkinson's disease and for various mutations associated with the amyloid β-peptide and responsible for either early-onset Alzheimer's disease or hereditary cerebral haemorrhage with amyloidosis (Table 2).

If the analysis is repeated using only one single determinant to calculate the $\ln(v_{mut}/v_{wt})$ values, significant correlations were still found between calculated and observed values of $\ln(v_{mut}/v_{wt})$ (p=0.0003 using only $\Delta$Hydr to calculate $\ln(v_{mut}/v_{wt})$, p=0.036 using only $\Delta\Delta G_{coil\text{-}\alpha}+\Delta\Delta G_{\beta\text{-}coil}$ and p=0.011 using only $\Delta$Charge). Nevertheless, these correlations are less remarkable than that observed when considering a combination of all three factors and the slopes are significantly less than 1.0 (0.61, 0.19 and 0.10 using only $\Delta$Hydr, only $\Delta\Delta G_{coil\text{-}\alpha}+\Delta\Delta G_{\beta\text{-}coil}$ and only $\Delta$Charge, respectively). This demonstrates that the equation in which these factors are combined gives a more accurate method for determining the ratio of rate of aggregation for modified (e.g. mutant) and reference (e.g. wild type) polypeptides.

The correlation shown in FIG. 2(a) between theoretical and experimental effects of mutations on aggregation was found to be striking, considering the heterogeneous group of protein and peptide systems used in the analysis as well as the variability of sites at which the various mutations occur.

Example 4

Applicability of the algorithm to modifications involving several amino acid residues and the use of kinetic parameters other than "aggregation rates".

Equation 1 was tested against other systems to evaluate its applicability to broader systems. Calculations used to derive Equation 1 are based on the aggregation kinetics experienced by protein and peptide variants that differ in a single residue from the original sequence. The rates ($v_{mut}$ and $v_{wt}$) used in the expression correspond to the exponential phase of aggregation for each one of the peptides, and do not include any possible lag period or nucleation phase preceding that stage.

To test the validity of this expression in predicting the aggregation propensities of peptides derived from two Calcitonin variations were included. The first was to evaluate if the effect of several substitutions could be predicted in the same manner the algorithm was able to do with single point mutations. The second was to include as a kinetic parameter the relative ratio of aggregation times ($\tau_{mut}/\tau_{wt}$). By including the effect of a lag phase on the kinetics of aggregation exhibited by the peptides, the aggregation times for each one of the peptides ($\tau$), could be defined in two different ways: the first one was the nucleation time or time that precedes the initiation of aggregation or the development of turbidity in the solution (T1), and the second one would correspond to the half time of aggregation or the time at which variations in the measurements used for monitoring aggregation (light scattering, or any other method) reached half of it maximum value (T2). This might enable the application of the equation to the prediction of aggregation propensities for a much broader range of molecules with important design aspects.

The calculations were made on two variants of Calcitonin, using data available in the literature (Arvinte, et al. 1993, J Biol Chem 268: 6415-6422), and previous studies included in another patent application by some of the members of the group (Zurdo & Dobson, WO 02/083734, PCT/GB02/01778). The calculations were made using data disclosed in those publications, producing the values indicated in table 3. In both cases the value for the $\tau_{wt}$ parameter was obtained independently.

TABLE 3

Predicted and experimental changes in times of
aggregation exhibited by various calcitonin peptides
when compared to the human sequence.

| | Calculated $\ln(v_{mut}/v_{wt})$ | Observed $\ln(v_{mut}/v_{wt})$ | Calculated $(\tau_{mut}/\tau_{wt})$ | Observed $(\tau_{mut}/\tau_{wt})$ |
|---|---|---|---|---|
| [1]Salmon-1 | −10.54 | −10.31 | 37,681.05 | ~30,000[a] |
| [2]SEQ ID NO 14 | −5.60 | −4.61[b]/−5.71[a] | 271.70 | 100[b]/300[a] |

[1]Data obtained from Arvinte et al. (1993) J Biol Chem 268, 6415-6422. Salmon calcitonin has 16 modified positions when compared to the human sequence.
[2]Sequence reported in Zurdo & Dobson (WO 02/083734, PCT/GB02/01778), and Zurdo & Dobson (unpublished observations). Sequence ID NO 14 show 6 modified positions when compared to the human sequence.
[a]Values for calculating τ were obtained using T1 as described above.
[b]Values for calculating τ were obtained using T2 as described above.

Calculations for changes in aggregations time were made assuming the following relations with aggregation rates described by equation 1.

$$(\tau_{mut}/\tau_{wt})=(v_{wt}/v_{mut})=1/\exp(\ln(v_{mut}/v_{wt}))$$

This analysis shows that equation 1 can be used to predict the aggregation behaviour of a given polypeptide that has more than one amino acid modification compared to the original polypeptide sequence. Moreover, it suggests that in systems where a lag phase is present, or the aggregation rate can be difficult to calculate, alternative kinetic parameters represented by the times of aggregation (either T1-nucleation time—or T2-half time of aggregation—) can provide valid values to compare with the predictions given by Equation 1.

Example 5

Applicability of the Algorithm to Modifications Involving Addition or Deletion of Amino Acid Residues: Aβ Peptides Linked With Alzheimer's Disease Peptides Aβ(1-40) and Aβ(1-42) that are associated with Alzheimer's disease show differences in their aggregation propensities. The peptides differ in sequence only by two residues at the C-terminus. The methods of the invention explain the higher propensity to aggregate of the 42 residues form, relative to the 40 residues form, of the amyloid β peptide associated with Alzheimer's disease (Jarrett et al., 1993). Indeed, although the (α-helical propensity and charge of the entire peptide appear to be unchanged upon addition of the dipeptide Ile-Ala at the C-terminus, the values of hydrophobicity and β-sheet propensity of the two residues are higher than the average values calculated over the entire peptide.

From a quantitative point of view, the change of hydrophobicity resulting from the addition of the two residues at the C-terminus can be calculated as $\Delta Hydr = Hydr_{wt} - Hydr_{mut}$, where $Hydr_{wt}$ is the average hydrophobicity of the 40 residues forming the short form of the peptide; $Hydr_{mut}$ is the average hydrophobicity of the two inserted residues (Ile-Ala). The change of β-sheet propensity resulting from insertion can be calculated similarly. This leads to the prediction that the long form aggregates 7 times faster than the short form, in good agreement with the kinetic profile reported by Jarrett et al., 1993 who found acceleration of 7-8 times (Jarrett J T, Berger E P, Lansbury P T Jr. The carboxy terminus of the beta amyloid protein is critical for the seeding of amyloid formation: implications for the pathogenesis of Alzheimer's disease. *Biochemistry*, 32, 4693-4697 (1993)).

Example 6

Computer System for Operating the Method of the Invention

Figure 3:
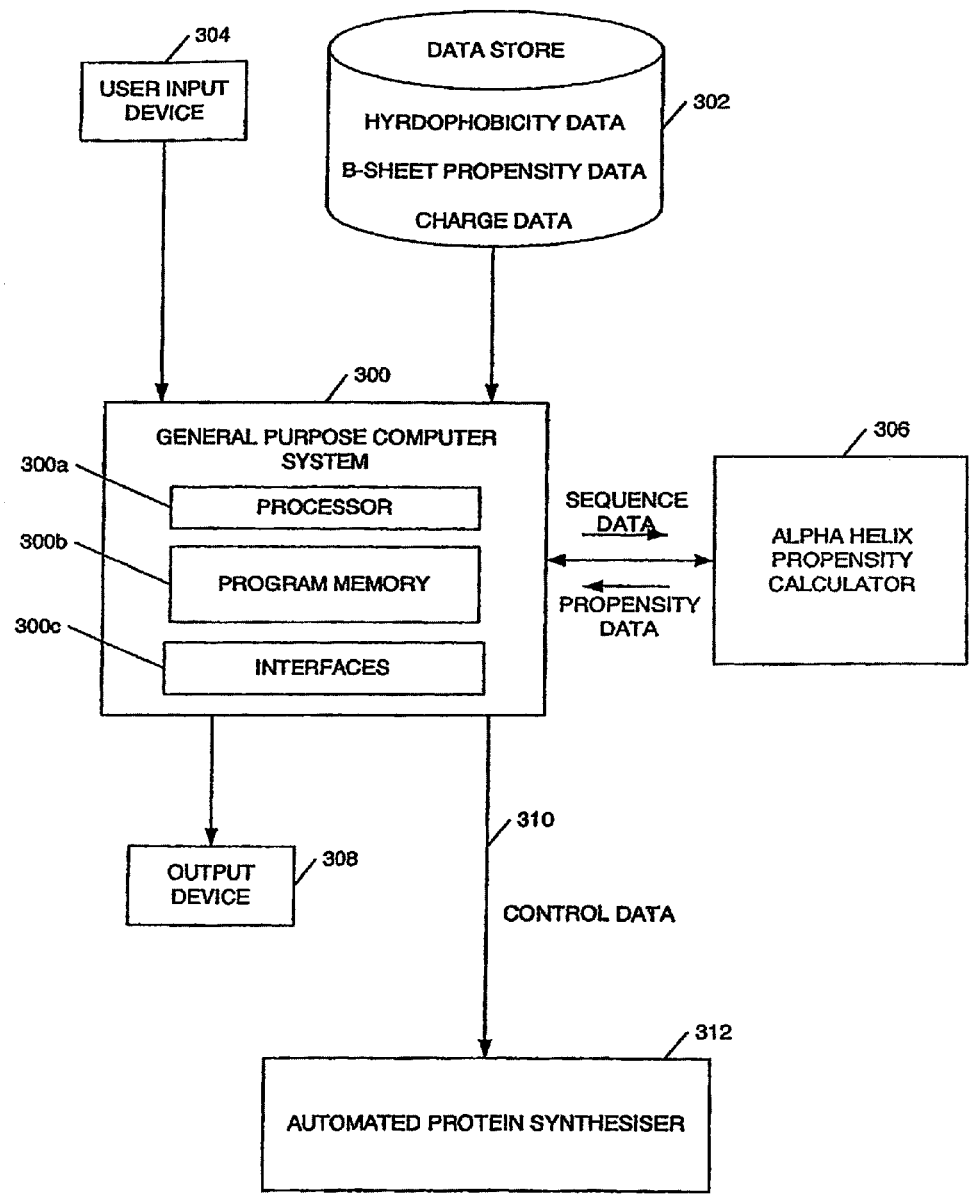
FIG. 3 shows a block diagram of a computer system for implementing an aggregation rate determination procedure according to an embodiment of an aspect of the present invention.

Referring now to FIG. 3, this shows a block diagram of a computer system for implementing an embodiment of the above-described method. A general purpose computer system 300 comprises a processor 300a coupled to programme memory 300b storing computer programme code to implement embodiments of the method, as described further below, and interfaces 300c such as conventional computer screen, keyboard, mouse, and printer, as well as other interfaces such as a network interface, a control interface for a peptide synthesiser and software interfaces such as a database interface.

The computer system 300 accepts user input from a input device 304 such as a keyboard, input data file, or network interface, and provides an output to an output device 308 such as a printer, network interface, or data storage device. Input device 304 receives an input comprising an amino acid sequence for the modified (e.g. mutant) peptide as well as pH and temperature values appropriate to an environment for which the aggregation rate of the polypeptide is determined. A glycine/proline correction factor, such as a weight for a structural distortion factor interfering with inter-molecular β-sheet formation or aggregation, may also be inputted. The output device 308 provides a comparative aggregation rate information such as a log (base 10 or natural) aggregation ratio, for example, a ratio of half times for aggregation of a mutant as compared with a wild type polypeptide.

Computer system 300 is coupled to a data store 302 which stores hydrophobicity data, β-sheet propensity data (either as propensity data per se or in terms of free energy) and charge data. This data is stored for each amino acid (residue) and preferably a plurality of sets of each of these data types is stored corresponding to different values of pH and temperature. The computer system, in the illustrated embodiment, is shown interfacing with an α-helix propensity calculator 306. This may be a separate machine, for example, coupled to computer system 300 over a network, or may comprise a separate programme running on general purpose computer system 300, or in other embodiments α-helix propensity code may be stored within programme memory 300b and operate in a unitary fashion with the aggregation rate determination code described below. However whichever method is employed the α-helix propensity calculator receives sequence data, indirectly from the user input device, and provides α-helix propensity data in return. This data and the data in data store 302 may either be determined on an amino acid by amino acid basis or may be determined taking into account sequence context, for example, using a window over the sequence to modify data values dependent upon neighbouring amino acids.

As illustrated, computer system 300 may also provide a data control output 310 to an automated peptide synthesiser 312. The control data will generally comprise an amino acid sequence of a polypeptide. In this way computer system 300 may be programmed to automatically compare the properties of a number of modified (e.g. mutant) polypeptides and select one or more of those which are predicted to have favourable properties for automated synthesis. An example of such an automated peptide synthesiser would be an ABI 433A Peptide Synthesiser (Applied Biosystems).

Figure 4:
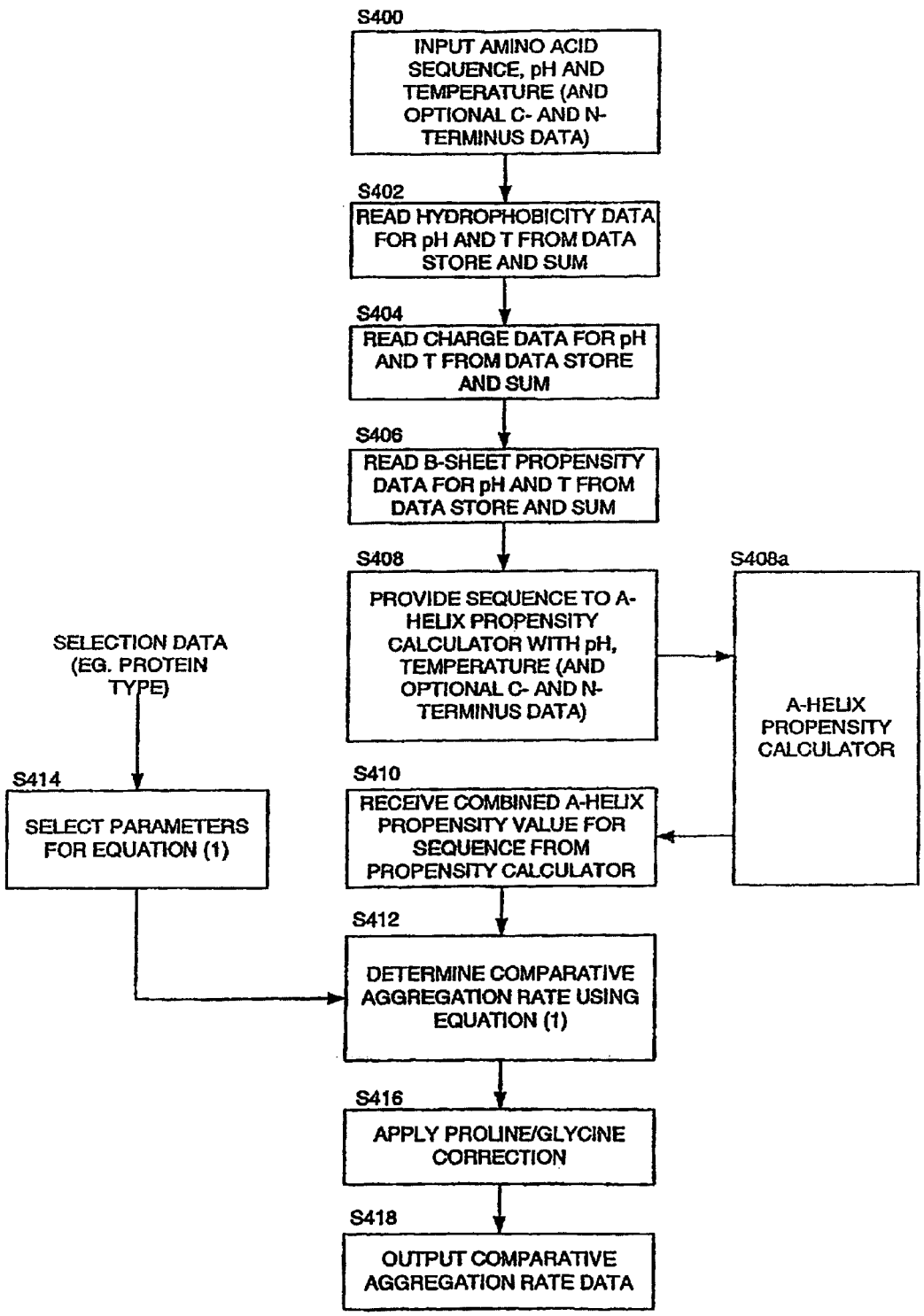
FIG. 4 shows a flow diagram of a comparative aggregation rate determination procedure according to an embodiment of the present invention.

Referring next to FIG. 4, this shows a procedure for determining a comparative aggregation rate along the lines described above. FIG. 4 represents a flow diagram of an embodiment of code running in programme memory 300b of FIG. 3.

At step S400 a user inputs an amino acid sequence, pH and temperature data, optionally with C- and N-terminus data for the sequence. Then at step S402 the computer system reads hydrophobicity data for the input sequence from the data store and sums this to provide an estimate of hydrophobicity for the peptide coded by the sequence. Where, as is strongly preferable, data for a range of pH and temperature values is available, data most closely corresponding to the desired pH and temperature is retrieved. Then as steps S404 and S406, the procedure reads charge data and β-sheet propensity data from the data store in a similar manner, summing the charge data to provide a charge estimate for the polypeptide corresponding to the input sequence and, similarly, summing the β-sheet propensity data (normally expressed in terms of free energy). With proline, no β-sheet propensity value is available and so a proline residue may be skipped when summarising these values or an arbitrary β-sheet propensity value or one corresponding to another amino acid may be employed. For example, if β-sheet propensity is expressed in terms of free energy, an arbitrary value of 1, or a value corresponding to another amino acid can be used. Optionally steps S402 and S406 may employ a "window" (for example of 3, 5, 7, or more amino acids) that would include a correction for the effect of flanking residues on the properties of a particular amino acid, (i.e. to take account of near neighbours within an amino acid sequence), rather than considering each amino acid of the sequence individually.

Step S408 the procedure provides the input sequence to an α-helix propensity calculator, with the pH and temperature data, and, where available, with the C- and N-terminus data. An α-helix propensity calculator S408a operates on this data and returns data back to the procedure at step S410, the returned data comprising an α-helix propensity value for the complete sequence. Suitable programme code for α-helix propensity calculator S408a comprises the AGADIR code available from http://www.embl-heidelberg.de/Services/serrano/agadir/agadir-start.html, GOR4 code available from http://npsa-pbil.ibcp.fr/cgi-bin/npsa_automat.pl?page=npsa_gor4.html and other codes described above. The skilled person will recognise that, if desired, this code or a newly designed code derived from publicly accessible (described in the scientific literature) or additional experimental data may be incorporated within the code implementing the procedure of FIG. 4 rather than being implemented as a separate procedure.

At step S412 the procedure then determines the comparative aggregation rate of the polypeptide defined by the input amino acid sequence as compared with a reference polypeptide, using equation 1 above. It can be seen from equation 1 that a determination of comparative aggregation rate requires a difference in hydrophobicity, secondary structural propensity, and charge, and values for hydrophobicity, secondary structural propensity and charge for the reference polypeptides may either be determined by repeating steps S400 to S410 for the reference polypeptide or by reading stored values of these parameters from data store 302, or in any other conventional manner. If desired at step S412 the parameters or scaling factors in equation 1 operating on the differences in hydrophobicity, structural propensity and charge can be selected from sets of suitable parameters (step S414) in response to input data such as polypeptide type data. For example, a completely random coil polypeptide may use different parameters to a partially unfolded or structured polypeptide. Also, a polypeptide rich in a specific type of residue, such as aromatic or charged amino acids, may require different parameters.

After determining the comparative aggregation rate an optional correction may be applied at step S416 for proline and or glycine residues in order to account for additional conformational or structural preferences that may hinder formation of inter-molecular β-sheet or aggregated structures by a given polypeptide and then at step S418 the system outputs the result of the comparative aggregation rate calculation. This may comprise a simple positive or negative value indicating whether the aggregation rate of the modified polypeptide (e.g. mutant) is greater or less than that of the reference polypeptide, but preferably this comprises quantitative data relating to the comparative aggregation rates such as a log aggregation rate ratio.

Figure 5:
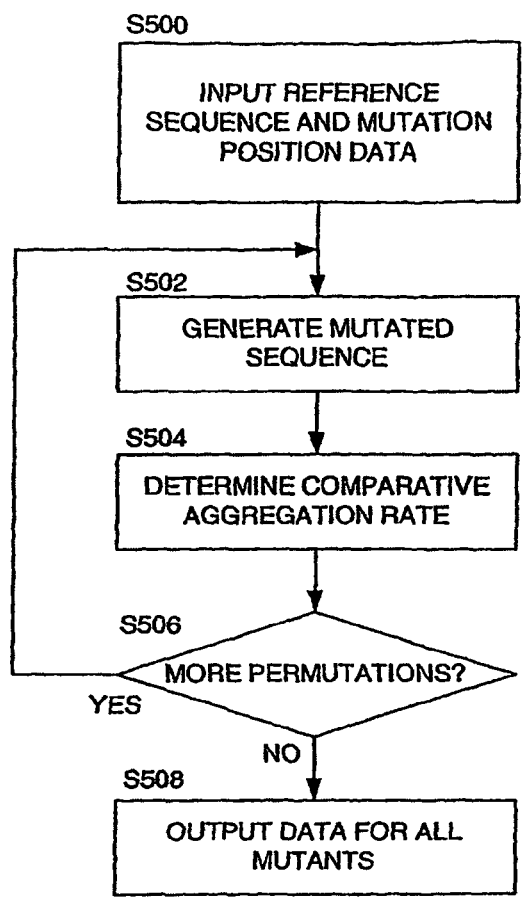
FIG. 5 shows a flow diagram of an automated protein synthesis candidate determination procedure.

FIG. 5 shows a flow diagram of one advantageous implementation of the procedure of FIG. 4. In particular FIG. 5 shows a method of screening modified polypeptides (e.g. mutations) in order to select candidates with promising properties for further investigation and, optionally, synthesis. Thus at step S500 an amino acid sequence-for a reference polypeptide is input together with data identifying one or more modified (e.g. mutant) positions. Optionally the procedure may also allow a modification or range of modifications to be specified, for example in terms of a pre-determined set or selection of amino acids.

Following initialisation, at step S502 the procedure generates a modified sequence representing one of the possible permutations defined by the input data and then, at step S504, determines a comparative aggregation rate for modified polypeptide in comparison with the reference polypeptide, for example using the procedure at FIG. 4. Then, at step S506, the procedure checks whether there are any more permutations for which to perform the calculation, and if so returns to step S502 until a complete set of possible permutations has been generated. Then, at step S508, the set of comparative aggregation rate data for each modified polypeptide (in comparison with the reference protein) is output, for example as an autolist, graph, or in any other convenient manner. This data may then be used, for example to identify candidates for synthesis and/or for comparison with other data such as immunogenicity/antigenicity. In particular, one or more of the 'best' modified polypeptides, for example mutants with a particularly high or low aggregation rate, may be collected and the sequence data for these modified polypeptides output to an automated peptide synthesiser such as synthesiser 312 of FIG. 3 to automatically produce the mutant proteins for, say, further investigation.

Bibliography

Dobson, C. M. Protein folding and its links with human disease. *Biochem. Soc. Symp.* 68, 1-26 (2001).

Jarrett, J. T., Berger, E. P. & Lansbury, P. T. Jr. The carboxy terminus of the beta amyloid protein is critical for the seeding of amyloid formation: implications for the pathogenesis of Alzheimer's disease. *Biochemistry* 32, 4693-4697.

Selkoe, D. J. Alzheimer's disease: genes, proteins, and therapy. *Physiol. Rev.* 81, 741-766 (2001).

Siepen, J. A. & Westhead, D. R. The fibril_one on-line database: Mutations, experimental conditions, and trends associated with amyloid fibril formation. Protein Sci. 11, 1862-1866 (2002).

Volles, M. J. & Lansbury, P. T. Jr. Vesicle permeabilization by protofibrillar (α-synuclein is sensitive to Parkinson's disease-linked mutations and occurs by a pore-like mechanism. *Biochemistry,* 41, 4595-4602 (2002).

For the following documents the numbers are those used in table 2:

11. Azriel, R. & Gazit, E. Analysis of the minimal amyloid-forming fragment of the islet amyloid polypeptide. An experimental support for the key role of the phenylalanine residue in amyloid formation. *J. Biol. Chem.* 276, 34156-34161 (2001).
12. Sakagashira, S., Hiddinga, H. J., Tateishi, K., Sanke, T., Hanabusa, T., Nanjo, K & Eberhardt, N. L. S20G mutant amylin exhibits increased in vitro amyloidogenicity and increased intracellular cytotoxicity compared to wild-type amylin. *Am. J. Pathol.* 157, 2101-2109 (2000).
13. Salmona, M., Malesani, P., De Gioia, L., Gorla, S., Bruschi, M., Molinari, A., Della Vedova, F., Pedrotti, B., Marrari, M. A., Awan, T., Bugiani, O., Forloni, G., Tagliavini, P. Molecular determinants of the physicochemical properties of a critical prion protein region comprising residues 106-126. *Biochem J.* 342, 207-214 (1999).
14. Thompson, A. J., Barnham, K. J., Norton, R. S., Barrow, C. J. The Val-210-Ile pathogenic Creutzfeldt-Jakob disease mutation increases both the helical and aggregation propensities of a sequence corresponding to helix-3 of PrP(C). Biochim. Biophys. Acta. 1544, 242-254 (2001).
15. Conway, K. A., Lee, S. J., Rochet, J. C., Ding, T. T., Williamson, R. E. & Lansbury, P. T. Jr. (2000). Acceleration of oligomerization, not fibrillization, is a shared property of both alpha-synuclein mutations linked to early-onset Parkinson's disease: implications for pathogenesis and therapy. *Proc. Natl. Acad. Sci. USA,* 97, 571-576.
16. Giasson, B. I., Murray, I. V., Trojanowski, J. Q. & Lee, V. M. A hydrophobic stretch of 12 amino acid residues in the middle of α-synuclein is essential for filament assembly. *J. Biol. Chem.* 276, 2380-2386 (2001).
17. Van Nostrand, W. E., Melchor, J. P., Cho, H. S., Greenberg, S. M. & Rebeck, G. W. (2001). Pathogenic effects of D23N Iowa mutant amyloid beta-protein. *J. Biol. Chem.* 276, 32860-32866.
18. Miravalle L, Tokuda T, Chiarle R, Giaccone G, Bugiani O, Tagliavini F, Frangione B, Ghiso J. J Biol Chem 2000 Sep. 1; 275(35):27110-6
19. Nilsberth, C., Westlind-Danielsson, A., Eckman, C. B., Condron, M. M., Axelman, K., Forsell, C., Stenh, C., Luthman, J., Teplow, D. B., Younkin, S. G., Naslund, J. & Lannfelt, L. (2001). The 'Arctic' APP mutation (E693G) causes Alzheimer's disease by enhanced Aβ protofibril formation. *Nature Neurosci.* 4, 887-893.
20. Esler, W. P., Stimson, E. R., Ghilardi, J. R., Lu, Y. A., Felix, A. M., Vinters, H. V., Mantyh, P. W., Lee, J. P. & Maggio, J. E. Point substitution in the central hydrophobic cluster of a human β-amyloid congener disrupts peptide folding and abolishes plaque competence. Biochemistry, 35, 13914-13921 (1996).
21. Barghorn, S., Zheng-Fischhofer, Q., Ackmann, M., Biernat, J., von Bergen, M., Mandelkow, E. M. & Mandelkow, E. (2000). Structure, microtubule interactions, and paired helical filament aggregation by tau mutants of frontotemporal dementias. *Biochemistry,* 39, 11714-11721.
22. Gamblin, T. C., King, M. B., Dawson, H., Vitek, M. P., Kuret, J., Berry, R. W., Binder, L. I. In vitro polymerization of tau protein monitored by laser light scattering: method and application to the study of FTDP-17 mutants. *Biochemistry,* 39, 6136-6144 (2000).
23. Nacharaju, P., Lewis, J., Easson, C., Yen, S., Hackett, J., Hutton, M. & Yen, S. H. Accelerated filament formation from tau protein with specific FTDP-17 missense mutations. *FEBS Lett.* 447, 195-199 (1999).
23b. Li, L., Von Bergen, M., Mandelkow, E. M. & Mandelkow, E. Structure, stability, and aggregation of paired helical filaments from tau protein and FTDP-17 mutants probed by tryptophan scanning mutagenesis. *J. Biol. Chem.* in press (2002).
24. Symmons, M. F., Buchanan, S. G., Clarke, D. T., Jones, G. & Gay, N. J. X-ray diffraction and far-UV CD studies of filaments formed by a leucine-rich repeat peptide: structural similarity to the amyloid fibrils of prions and Alzheimer's disease β-protein. *FEBS Lett.* 412, 397-403 (1997).
25. Orpiszewski, J. & Benson, M. D. Induction of beta-sheet structure in amyloidogenic peptides by neutralization of aspartate: a model for amyloid nucleation. *J. Mol. Biol.* 289, 413-428 (1999).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. An in silico method of determining a relative aggregation rate indicator, said relative aggregation rate indicator predicting a rate of aggregation of a second polypeptide based upon its amino acid seqeuence in comparison to a rate of aggregation of a reference polypeptide, said second polypeptide comprising one or more amino acid modification(s) when compared to the reference polypeptide, the method comprising using one or more processors to:
- determine a difference in hydrophobicity between said second polypeptide and said reference polypeptide;
- determine a difference in a secondary structure propensity between said second polypeptide and said reference polypeptide;
- determine a difference in charge between said second polypeptide and said reference polypeptide;
- form a weighted combination of said difference in hydrophobicity, said difference in secondary structure propensity, and said difference in charge to determine said relative aggregation rate indicator by summing each said difference multiplied by a scaling factor;
- wherein said scaling factors used in said weighted combination are selected in response to data on said reference polypeptide.

2. A method as claimed in claim 1 wherein said weighted combination comprises a linear combination.

3. A method as claimed in claim 1 wherein said relative aggregation rate indicator comprises a logarithm of a ratio of aggregation rates of said second and reference polypeptides.

4. A method as claimed in claim 1 further comprising determining weights for said weighted combination using known aggregation rates for mutations of said reference polypeptide.

5. A method as claimed in claim 1 wherein said secondary structure propensity comprises a propensity to convert from an α-helical to a β-sheet structure.

6. A method of selecting a polypeptide for synthesis comprising:
- creating a set of candidate polypeptides from a reference polypeptide sequence;
- determining a relative rate of aggregation for each of said candidates using the method of claim 1; and
- selecting a said candidate for synthesis dependent upon the result of said relative aggregation rate determining.

7. The method according to claim 6, wherein creating a set of candidate polypeptides comprises synthesizing said selected candidate for synthesis.

8. The method according to claim 1, wherein the weighted combination is formed using $[x*\Delta Hydr]+[y*(\Delta\Delta G_{coil-\alpha}+\Delta\Delta G_{\beta-coil})]-[z*\Delta Charge]$ wherein x, y and z are scaling factors, ($\Delta Hydr$) is the difference in hydrophobicity, $\Delta\Delta G_{coil-\alpha}+\Delta\Delta G_{\beta-coil}$ is the difference in a secondary structure propensity and $\Delta Charge$ is the difference in charge.

9. The method according to claim 8, wherein the scaling factor x is a value from 0.59 to 0.64, the scaling factor y is a value from 0.19 9to 0.22 and the scaling factor z is a value from 0.49 to 0.51.

10. The method according to claim 8, wherein x is 0.6, y is 0.2 and z is 0.5.

11. The method according to claim 8, wherein x is 0.63, y is 0.20 and z is 0.49.

12. The method according to claim 1, wherein the scaling factors are found using a multiple regression analysis by calculating simultaneously each scaling factor for said reference polypeptide for which experimental values of aggregation rate are available.

13. The method according to claim 12, wherein initial estimates for each scaling factor are chosen on an arbitrary basis.

14. The method according to claim 12, comprising repeating the calculating step through a number of iterations until a set of best values for said scaling factors is found.

* * * * *

UNITED STATES PATENT AND TRADEMARK OFFICE
CERTIFICATE OF CORRECTION

PATENT NO. : 8,849,578 B2  Page 1 of 1
APPLICATION NO. : 12/061489
DATED : September 30, 2014
INVENTOR(S) : Dobson et al.

It is certified that error appears in the above-identified patent and that said Letters Patent is hereby corrected as shown below:

In the Claims,

In column 25, line 15, in Claim 1, delete "seqeuence" and insert --sequence--, therefor In column 26, line 30, in Claim 9, delete "9to" and insert --to--, therefor Signed and Sealed this
Fifteenth Day of September, 2015

Michelle K. Lee
*Director of the United States Patent and Trademark Office*